United States Patent
Bispo et al.

(10) Patent No.: US 12,195,810 B2
(45) Date of Patent: Jan. 14, 2025

(54) COMPREHENSIVE MICROBIAL PANEL FOR MOLECULAR DIAGNOSIS OF EYE INFECTIONS

(71) Applicant: Massachusetts Eye and Ear Infirmary, Boston, MA (US)

(72) Inventors: Paulo Jose Martins Bispo, Cambridge, MA (US); Michael S. Gilmore, Boston, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 550 days.

(21) Appl. No.: 16/955,640

(22) PCT Filed: Dec. 20, 2018

(86) PCT No.: PCT/US2018/066836
§ 371 (c)(1),
(2) Date: Jun. 18, 2020

(87) PCT Pub. No.: WO2019/126523
PCT Pub. Date: Jun. 27, 2019

(65) Prior Publication Data
US 2020/0385818 A1 Dec. 10, 2020

Related U.S. Application Data

(60) Provisional application No. 62/610,012, filed on Dec. 22, 2017.

(51) Int. Cl.
*C12Q 1/6888* (2018.01)
*C12Q 1/70* (2006.01)

(52) U.S. Cl.
CPC .......... *C12Q 1/6888* (2013.01); *C12Q 1/705* (2013.01); *C12Q 2600/106* (2013.01); *C12Q 2600/16* (2013.01)

(58) Field of Classification Search
None
See application file for complete search history.

(56) References Cited

U.S. PATENT DOCUMENTS

2010/0129391 A1  5/2010  Reed et al.
2017/0275710 A1  9/2017  Rao et al.

FOREIGN PATENT DOCUMENTS

WO   WO 03/087353   10/2003

OTHER PUBLICATIONS

Barczak et al., "RNA signatures allow rapid identification of pathogens and antibiotic susceptibilities," Proc. Natl. Acad. Sci. USA, Apr. 2012, 109(16):6217-6222.
Bispo et al., "Pignatari AC. Detection and gram discrimination of bacterial pathogens from aqueous and vitreous humor using real-time," PCR Assays. Invest. Ophthalmol. Vis. Sci., Feb. 2011, 52(2):873-881.
Dabil et al., "Validation of a diagnostic multiplex polymerase chain reaction assay for infectious posterior uveitis," Arch. Ophthalmol, Sep. 2001, 119(9):1315-1322.
Groot-Mijnes et al., "Polymerase chain reaction and Goldmann-Witmer coefficient analysis are complimentary for the diagnosis of infectious uveitis," Am. J. Ophthalmol, Feb. 2006;141(2):313-318.
Harper et al., "Polymerase chain reaction analysis of aqueous and vitreous specimens in the diagnosis of posterior segment infectious uveitis," Am. J. Ophthalmol, Jan. 2009, 147(1):140-147.
PCT International Preliminary Report on Patentability in International Appln. No. PCT/US2018/066836, dated Jun. 23, 2020, 11 pages.
PCT International Search Report and Written Opinion in International Appln. No. PCT/US2018/066836, dated Jun. 17, 2019, 21 pages.
Sugita et al., "Use of a comprehensive polymerase chain reaction system for diagnosis of ocular infectious diseases," Ophthalmology, Sep. 2013,120(9):1761-1768.
Sugita et al., "Use of multiplex PCR and real-time PCR to detect human herpes virus genome in ocular fluids of patients with uveitis," Br. J. Ophthalmol., Jul. 2008, 92(7):928-932.
Taravati et al., "Role of molecular diagnostics in ocular microbiology," Curr. Ophthalmol. Rep., Dec. 2013, 1(4):181-189.
Bispo et al., "Detection and gram discrimination of bacterial pathogens from aqueous and vitreous humor using real-time," PCR Assays. Invest. Ophthalmol. Vis. Sci., Feb. 2011, 52(2):873-881.

*Primary Examiner* — Carolyn L Greene
(74) *Attorney, Agent, or Firm* — Fish & Richardson P.C.

(57) ABSTRACT

Methods for sensitive and reliable qualitative detection and identification of the common pathogens associated with ocular infections, including uveitis, endophthalmitis and keratitis.

9 Claims, 3 Drawing Sheets
Specification includes a Sequence Listing.

COMPREHENSIVE MICROBIAL PANEL FOR MOLECULAR DIAGNOSIS OF EYE INFECTIONS

CLAIM OF PRIORITY

This application is a U.S. National Stage Entry of PCT/US2018/066836, filed on Dec. 20, 2018, which claims the benefit of U.S. Patent Application Ser. No. 62/610,012, filed on Dec. 22, 2017. The entire contents of the foregoing are hereby incorporated by reference.

SEQUENCE LISTING

The instant application contains a Sequence Listing which has been submitted electronically in ASCII format and is hereby incorporated by reference in its entirety. Said ASCII copy, created on May 29, 2020, is named SequenceListing.txt and is 23,255 bytes in size.

TECHNICAL FIELD

Described herein are kits, devices, and methods for diagnosing eye infections.

BACKGROUND

Eye infections are among the greatest causes of blindness worldwide. The sooner effective therapy can be started, the more vision that can be saved. In an era of increasing resistance, broad-spectrum antibiotics can no longer be relied upon.

SUMMARY

New technologies have the potential to significantly increase diagnostic sensitivity and quickly detect the microbe causing an infection, as well as its antibiotic resistance, providing the physician with critical information in hours, rather than days, and for a greater number of patients. The newly developed comprehensive eye panel described here is expected to support rapid treatment with the correct drug, which will limit the often-irreversible destruction that results in loss of vision.

Provided herein are methods comprising: providing a sample comprising, or suspected of comprising, a pathogen; optionally purifying genomic DNA from the pathogen; performing PCR by contacting the sample with a plurality of sets of primers to amplify each of at least 10, 20, 30, 40, or all of the target sequences listed in Table 1 (or its complement) in genomic DNA from the pathogen; and contacting the amplified DNA with a plurality of detectable probes, wherein the plurality comprises 1, 2, or more detectable probes that bind to each of the target sequences listed in Table 1 (or its complement).

Also provided are methods for determining identity of a pathogen in a sample, the method comprising: providing a sample comprising, or suspected of comprising, a pathogen; optionally purifying genomic DNA from the pathogen; performing PCR by contacting the sample with a plurality of sets of primers to amplify each of at least 10, 20, 30, 40, or all of the target sequences listed in Table 1 (or its complement) in genomic DNA from the pathogen; and contacting the amplified DNA with a plurality of detectable probes, wherein the plurality comprises 1, 2, or more detectable probes that bind to each of the target sequences listed in Table 1 (or its complement); detecting binding of the 1, 2, or more probes to the amplified DNA; determining the identity of the probes bound to the amplified DNA; and correlating the identity of the bound probes to a pathogen.

In addition, provided herein are methods for diagnosing an infection in a subject who has uveitis or detecting the presence of a pathogen in a subject who has uveitis. The methods include providing a sample from an eye of the subject comprising, or suspected of comprising, a pathogen; optionally purifying genomic DNA from the pathogen; performing PCR by contacting the sample with a plurality of sets of primers to amplify each of at least 10, 20, 30, 40, or all of the target sequences listed in Table 1 (or its complement) in genomic DNA from the pathogen; and contacting the amplified DNA with a plurality of detectable probes, wherein the plurality comprises 1, 2, or more detectable probes that bind to each of the target sequences listed in Table 1 (or its complement); detecting binding of the 1, 2, or more probes to the amplified DNA; determining the identity of the probes bound to the amplified DNA; and correlating the identity of the bound probes to a pathogen, thereby diagnosing the infection in the subject or identifying the pathogen.

Further, provided herein are methods for selecting a treatment and optionally treating a subject who has uveitis, the methods comprising: providing a sample from an eye of the subject comprising, or suspected of comprising, a pathogen; optionally purifying genomic DNA from the pathogen; performing PCR by contacting the sample with a plurality of sets of primers to amplify each of at least 10, 20, 30, 40, or all of the target sequences listed in Table 1 (or its complement) in genomic DNA from the pathogen; and contacting the amplified DNA with a plurality of detectable probes, wherein the plurality comprises 1, 2, or more detectable probes that bind to each of the target sequences listed in Table 1 (or its complement); detecting binding of the 1, 2, or more probes to the amplified DNA; determining the identity of the probes bound to the amplified DNA; and correlating the identity of the bound probes to a pathogen; and selecting and optionally administering to the subject a treatment for the pathogen, preferably wherein the treatment is selected according to Table A.

In some embodiments of the methods described herein, determining the sequence identity comprises using high resolution melting analysis.

In some embodiments of the methods described herein, the sequence identity of the amplified portion is correlated to a pathogen according to table 1.

In some embodiments of the methods described herein, the sample comprises aqueous humor, vitreous humor, or vitreous wash.

Also provided herein is a kit for use in a method described herein comprising: a plurality of sets of primers that amplify each of at least 10, 20, 30, 40, or all of the target sequences listed in Table 1 (or its complement); a plurality of probes that bind to each of the at least 10, 20, 30, 40, or all of the target sequences listed in Table 1 (or its complement), preferably wherein the plurality comprises at least 2 probes that bind to each of the target sequences; and optionally one or more reagents for performing a multiplexed gene analysis method, e.g., a hybridization based digital barcode quantification assays.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used.

The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
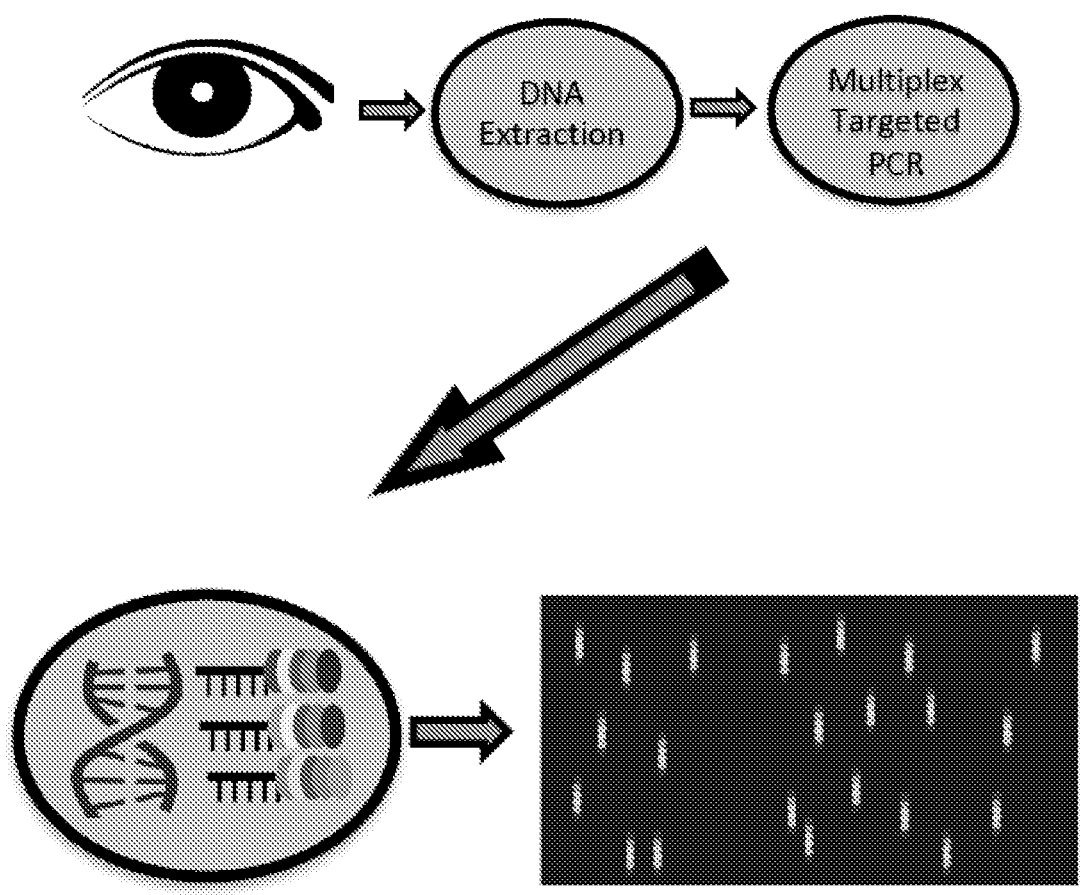
FIG. 1 provides an exemplary workflow for a method described herein.

Presently, infections of the eye are typically treated empirically with an antibiotic or antiviral depending on the initial clinical evaluations until a definitive diagnosis is returned from the clinical microbiology laboratory. Because many ocular pathogens cannot be readily cultured, and because of the small sample size, after several days of effort, a culture report is often returned as negative despite clear evidence of an infection in the patient. Time delays and low sensitivity of pathogen detection result in patients being treated empirically or with the wrong drug for long periods. In the interim, the infection continues its destructive path—much of it preventable if the pathogen and its susceptibilities had been more quickly identified. For these reasons, there is considerable interest in molecular detection of eye pathogens directly from ocular tissues, which has shown to significantly improve diagnosis sensitivity[1-7]. Previously, detection was mainly done by regular monoplex PCR assays for detection of one target at a time, or by multiplex PCR tests that are constricted by the number of fluorescent agents that current real time PCR systems can detect at the same time.

Described herein are unique multiplex panels for sensitive, accurate, and rapid diagnosis of sight-threatening ocular infections, including uveitis, endophthalmitis and keratitis, which can be implemented using commercially-available technology such as the molecular barcoding platform NanoString. The present methods provide an unparalleled possibility for comprehensive detection of the most clinically relevant organisms that cause eye infections in just one assay. By consolidating the detection of bacteria, viruses, fungi and parasites in only one platform, the use of this panel will not only save time on detection, but also spare precious small-volume ocular specimens. The detection of a variety of organisms that otherwise would require the use of multiple specific diagnostic tests, and a relatively high volume of sample, is possible with only a tiny ocular specimen in a single reaction. In addition to being uniquely designed to detect the most important ocular pathogens in a multiplex fashion, identification of pathogen DNA takes place in a highly sensitive platform for nucleic acid detection, which is expected to considerably improve the diagnostic sensitivities. Combined, the advantages of this panel is expected to greatly impact the clinical course of eye infections by supporting quick treatment with the correct drug, which will limit the often-irreversible destruction that results in loss of vision.

Methods of Diagnosis

Included herein are methods for sensitive and reliable qualitative detection and identification of the common pathogens associated with ocular infections, including uveitis, endophthalmitis and keratitis, including those shown in Table 1, directly from intraocular fluids in a single closed-tube reaction and methods of treatment based thereon. The methods include obtaining a sample comprising intraocular fluid from a subject, e.g., a sample comprising aqueous humor, vitreous humor, or vitreous wash, and evaluating the presence and/or level of a biomarker in the sample. Vitreous wash is the mix of vitreous and balanced salt solution that collects in the cassette of the vitrectomy machine during vitrectomy surgery, i.e., diluted vitreous humor. The sample can be obtained, e.g., by anterior paracentesis (aqueous samples), posterior chamber paracentesis (undiluted vitreous samples), or during pars plana vitrectomy (both undiluted vitreous and diluted vitreous washing samples).

The methods can optionally include comparing the presence and/or level of one or more of the biomarkers that can be used to determine the presence of a pathogen as described herein with one or more references, e.g., a control reference that represents a normal level of the biomarker e.g., a level in an unaffected subject, and/or a disease reference that represents a level of the biomarker associated with a specific infection, e.g., a level in a subject having an infection with a pathogen listed in Table 1. In some embodiments, the detection of any level of pathogen DNA indicates the presence of an infection with that pathogen.

The methods include first amplifying any sequences listed in Table 1 that are present in the sample using methods known in the art, e.g., using polymerase chain reaction (PCR), reverse transcriptase polymerase chain reaction (RT-PCR), quantitative or semi-quantitative real-time RT-PCR, or digital PCR i.e. BEAMing ((Beads, Emulsion, Amplification, Magnetics) Diehl (2006) Nat Methods 3:551-559), e.g., using primers that amplify each of the followed by sequence identity analysis.

The presence of a sequence listed in Table 1 can be evaluated using methods known in the art, e.g., using polymerase chain reaction (PCR), reverse transcriptase polymerase chain reaction (RT-PCR), quantitative or semi-quantitative real-time RT-PCR, digital PCR i.e. BEAMing ((Beads, Emulsion, Amplification, Magnetics), Diehl (2006) Nat Methods 3:551-559); various types of nucleic acid sequencing (Sanger, pyrosequencing, NextGeneration Sequencing); multiplexed gene analysis methods, e.g., oligo hybridization assays including DNA microarrays; hybridization based digital barcode quantification assays such as the nCounter® System (NanoString Technologies, Inc., Seattle, WA; Kulkarni, Curr Protoc Mol Biol. 2011 April; Chapter 25:Unit25B.10) and lysate based hybridization assays utilizing branched DNA signal amplification such as the QuantiGene 2.0 Single Plex and Multiplex Assays (Affymetrix, Inc., Santa Clara, CA; see, e.g., Linton et al., J Mol Diagn. 2012 May-June; 14(3):223-32); SAGE, high-throughput sequencing, multiplex PCR, MLPA, luminex/XMAP, or branched DNA analysis methods. See, e.g., WO2012/048113, which is incorporated herein by reference in its entirety.

In some embodiments, the level of one or more of the biomarkers evaluated is comparable to or above the level of the biomarker in a disease reference, then the subject can be diagnosed with an infection with the pathogen associated with the biomarker. In some embodiments, once it has been determined that a person has an infection with an identified pathogen, then a treatment, e.g., as known in the art or as described herein, can be administered.

Suitable reference values can be determined using methods known in the art, e.g., using standard clinical trial methodology and statistical analysis. The reference values can have any relevant form. In some cases, the reference comprises a predetermined value for a meaningful level of the biomarker, e.g., a control reference level that represents a normal level of the biomarker, e.g., a disease reference that represents a level of the biomarker associated with a specific infection.

The predetermined level can be a single cut-off (threshold) value, such as a median or mean, or a level that defines the boundaries of an upper or lower quartile, tertile, or other segment of a clinical trial population that is determined to be statistically different from the other segments. It can be a range of cut-off (or threshold) values, such as a confidence interval. It can be established based upon comparative groups, such as where association with risk of developing disease or presence of disease in one defined group is a fold higher, or lower, (e.g., approximately 2-fold, 4-fold, 8-fold, 16-fold or more) than the risk or presence of disease in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest into n-quantiles being subjects with the lowest risk and the highest of the n-quantiles being subjects with the highest risk.

In some embodiments, the predetermined level is based on the level of detection of the assay used, and a level of the biomarker above the level of detection indicates the presence of the pathogen associated with that biomarker.

In preferred embodiments, one, two, or more detectable probes (e.g., probes that are detectable using a multiplex gene analysis method as known in the art and/or described above) that bind to each of the sequences listed in Table 1 are used in the present methods. In embodiments where two or more probes for each sequence are used, the number of false positives can be limited by requiring detection of binding of both probes in order to determine that a sequence is present in the sample.

Targeted Treatment

Once the presence of a specific pathogen has been identified using a method described herein, the method can include selecting and optionally administering a treatment specific for that pathogen as known in the art. For example, a treatment according the following Table A can be selected and/or administered:

TABLE A

| Pathogen | Treatment |
| --- | --- |
| Herpes simplex virus 1 or 2 (HSV1/2) | Systemic antiviral therapy (e.g., acyclovir, famciclovir, or valacyclovir) for uveitis and keratitis<br>Intravitreal foscarnet or ganciclovir for uveitis<br>Topical ganciclovir gel, trifluridine and acyclovir ointments for keratitis |
| Cytomegalovirus (CMV) | Oral or IV antiviral therapy (e.g., valganciclovir, ganciclovir, foscarnet, or cidofovir)<br>Intravitreal foscarnet or ganciclovir for uveitis<br>Topical ganciclovir gel for keratitis |
| Varicella zoster virus (VZV) | Oral or IV antiviral therapy (e.g., acyclovir, famciclovir, valacyclovir) for uveitis and keratitis<br>Intravitreal foscarnet or ganciclovir for uveitis |
| Epstein-barr virus (EBV) | Acyclovir, ganciclovir, valacyclovir and foscarnet |
| *Toxoplasma gondii* (*T. gondii*) | Monotherapy or combination therapy with systemic antimicrobials. The most commonly used are sulfadiazine, Bactrim, spiramycin, clindamycin, pyrimethamine, atovaquone, andr azithromycin. The traditional gold standard regimen has been triple drug therapy with pyrimethamine (loading dose of 75-100 mg during the first day, followed by 25-50 mg on subsequent days), sulfadiazine (loading dose of 2-4 g during the first 24 h followed by 1 g qid), and prednisone. Intravitreal clindamycin is also used in some cases. |
| Gram-positive cocci | Intravitreal vancomycin (1 mg) for endophthalmitis. Systemic antibiotics (e.g. linezolid and moxifloxacin) can be used.<br>Topical cefazolin (50 mg/ml), tobramycin or gentamicin (9-14 mg/ml) vancomycin (15-50 mg/ml), bacitracin (10,000 IU) and fluoroquinolones (0.3% to 0.5%) for keratitis |
| *Methicillin-resistant S. aureus* | Intravitreal vancomycin (1 mg) for endophthalmitis.<br>Topical cefazolin (50 mg/ml), tobramycin or gentamicin (9-14 mg/ml) vancomycin (15-50 mg/ml) or bacitracin (10,000 IU) for keratitis. Linezolid and daptomycin could also be used for treatment of both infections. |
| Gram-negative bacilli | Intravitreal ceftazidime (2.25 mg) or amikacin (0.1 mg) for endophthalmitis. Systemic antibiotics (e.g. moxifloxacin) can be used. Topical tobramycin or gentamicin (9-14 mg/ml), ceftazidime (50 mg/ml) and fluoroquinolones (0.3% to 0.5%) for keratitis |
| *Candida* spp. | Intravitreal amphotericin B (5 to 10 µg) or voriconazole (100 µg) plus systemic therapy with amphotericin, fluconazole or voriconazole and flucytosine for endophthalmitis. Oral fluconazole. Topical amphotericin B solution or flucytosine, fluconazole and itraconazole for keratitis. |

TABLE A-continued

| Pathogen | Treatment |
|---|---|
| *Aspergillus* spp. | Intracameral amphotericin (5 µg) or voriconazole (50 µg) and intravitreal amphotericin (5 to 10 µg) or voriconazole (100 µg), plus systemic voriconazole for endophthalmitis. Oral itraconazole or voriconazole. Topical natamycin, amphotericin B, or flucytosine, fluconazole and itraconazole for keratitis. Topical voriconazole can be used for recalcitrant cases. |
| *Fusarium* spp. | Intracameral amphotericin (5 µg) or voriconazole (50 µg) and intravitreal amphotericin (5 to 10 µg) or voriconazole (100 µg), plus systemic voriconazole for endophthalmitis. Oral itraconazole or voriconazole. Topical natamycin or flucytosine, fluconazole and itraconazole for keratitis. Topical voriconazole can be used for recalcitrant cases. |
| *Mycobacterium tuberculosis* | Isoniazid 5 mg/kg/day, rifampicin 450 mg/day if body weight is <50 kg and 600 mg if the weight is >50 kg, ethambutol 15 mg/kg/day, and pyrazinamide 25-30 mg/kg/day) for 8 weeks, followed by two drugs (rifampicin and isoniazid) for at least another 18 weeks |
| *Treponema pallidum* | Intravenous penicillin (4 million units every 4 h for 10 to 14 days) |
| *Borrelia burgdorferi* | Intravenous ceftriaxone (2 g daily from 10 to 28 days) is the preferred therapy. Alternative includes intravenous penicillin G (15 to 20 million units daily for 10 to 14 days) and oral doxycycline (2 weeks) |
| *Tropheryma whipplei* | Intravenous therapy ceftriaxone (2 g daily for 2-4 weeks) or meropenem. Oral trimethoprim-sulfamethoxazole and doxycycline |

Kits

Included herein are kits that can be used in the present methods. The kits can include containers holding one or more of the primers, e.g., pairs of primers that can be used to amplify each of the sequences shown in Table 1, one or more detectable probes that bind to each of the sequences shown in Table 1, as well as one or more reagents for performing the method, e.g., reagents for use in multiplexed gene analysis methods as described herein or known in the art.

Examples

The invention is further described in the following examples, which do not limit the scope of the invention described in the claims.

Methods

Selection of target sequences and panel design. Using sources including epidemiological information on the etiologies of ocular infections seen at our hospital, we identified 46 pathogens and 2 resistant/virulence markers that are commonly associated with ocular infections. This panel of organisms (Table 1) accounts for >90% of pathogens isolated from eye specimens. Genomic targets commonly used for PCR-based detection of these pathogens were scrutinized for stretches that are predicted to be specific for a particular species while being conserved across different strains from the same species. Regions of 150 to 300 bp in length were selected and a set of primers for pre-enrichment, and two 50 mer probes per target were designed to these sequences in collaboration with NanoString to incorporate their proprietary barcode sequences and bioinformatics algorithms to design probes that minimize cross-reactivity, and select probes with optimal thermodynamic profiles for optimized hybridization.

TABLE 1

| Target | Gene | Target Sequence | # |
|---|---|---|---|
| Gram positive rods and cocci | | | |
| *Bacillus cereus* group | RNA polymerase subunit B (rpoB) | GAATGCAAAGAGCGTGATGTGACGTATGCAGCACCACTTC GTGTAAAAGTGCGTCTAATCAACAAGGAAACTGGTGAAGT AAAAGAACAAGATGTGTTCATGGGAGATTTCCCACTCATG ACAGAGACTGGAACATTCGTAATTAACGGTGCAGAACGTG TTATCGTTTCCCAGTTAGTTCGCTCTCCAAGCGTATACTATA GTGGCAAAGTGGATAAAAACGGAAAACGTGGTTTTACTGC TACTGTAATTCCAAACCGCGGAGCTTGGTTAGAGTATGA | 1 |
| *Bacillus subtilis* group | 23S ribosomal subunit | CCCAGGCGACTGTTTAGCAAAAACACAGGTCTCTGCGAAG CCGTAAGGCGAAGTATAGGGGCTGACGCCTGCCCGGTGCT GGAAGGTTAAGAGGAGCGCTTAGCGTAAGCGAAGGTGCGA ATTGAAGCCCCAGTAAACGGCGGCCGTAACTATAACGGTC CTAAGGTAGCGAAATTCCTTGTCGGGTAAGTTCCGACCCGC ACGAAAGGCGCAACGATCTGGGCACTGTCTCAACGAGAGA CTCGGTGAAATTAT | 2 |
| *Enterococcus faecalis* | D-Ala:D-Ala ligase (ddl) | TAGAAAGCGACATCTTTCACCACTTCACCAGGTAAAGTCGT ACGGACATCTTCATTTCCTAAAATGGCTACTTCAATTTCAC GTGCTTCGATCCCTTGTTCAACAATTGCTCGGGCATCATAA CGGAAAGCTTCTTCCAATGCTTCTTGCAATTCTTCACGATTT TCCACTTTGCTAATTCCGACACTAGAACCCATATTGGCAGG | 3 |

TABLE 1-continued

| Target | Gene | Target Sequence | # |
|---|---|---|---|
| | | TTTAACAAAGACCGGATAAATTAAAGAACCTTCACATTTTT CAAAGACTTCTTTTGGATTTCCTTTCCAGTCACTTCTTAAAA CTGGCACGAAT | |
| Enterococcus faecium | D-Ala:D-Ala ligase (ddl) | TTATTCATTTTTTTCAAAAAAAGATTGACGCTGATGGTATC GATTCATTCCTAACTGGATCAGTTCTTCAATCAAATCACCG TATTTCAAGCCCATATTTTCCCATAAGAGTGGGTACATACT GAACTCCGTAAATCCTGGCATAGAGTTTAATTCATTCAGGA ATAATTCATTTTTATTTGTCAAAAAGAAATCGCACCGGCTC AATCCGCTTCCACCTAACATCGTGTAAGCTAACTTCGCGTA CTCTTGCGCTTTTTGATAAACTTCTTCTGGCACTTCGGCTGG AATCTGCATTTC | 4 |
| Mycobacterium tuberculosis | Immunogenic protein MPT64 (mpt64) | CCGTGGTGCTCAAGGTCTACCAGAACGCCGGCGGCACGCA CCCAACGACCACGTACAAGGCCTTCGATTGGGACCAGGCC TATCGCAAGCCAATCACCTATGACACGCTGTGGCAGGCTGA CACCGATCCGCTGCCAGTCGTCTTCCCCATTGTGCAAGGTG AACTGAGCAAGCAGACCGGACAACAGGTATCGATAGCGCC GAATGCCGGCTTGGACCCGGTGAATTATCAGAACTTCGCAG TCACGAACGACGGGGTGATTTTCTTCTTCAACCCGGGGGAG TTGCTGCCCGAAGCAG | 5 |
| Propionibacterium acnes | Triacylglycerol lipase precursor | ATGAAGATCAACGCACGATTCGCCGTCATGGCCGCGAGTG TGGCCGTCCTGATGGCTGCCGCGCCGATTGCGCAGGCTGCT ACTTCGCCGGGGGATATCCATCCCCTGGTCCAGGCAGCCCA CAGCCCCGACGGTATTCCCGGTAACGGCGTCGGGCCGGAA TTCCATACGTCGTCGATGGCGCGTTCCTACAGCGAGAAGCA CCTGGGCGTGGCGCCGCGGGGTGTGAACGACTTCTCCTGCA AGGTCAAGCCCGGCGACCGACCGGTCATCCTGATTCCCGGT ACTGGCGGCAATGCG | 6 |
| Staphylococcus spp. | 23S ribosomal subunit | AGTATTTGGTCGTAGACCCGAAACCAGGTGATCTACCCWT GGTCAGGTTGAAGTTCAGGTAACACTGAATGGAGGACCGA ACCGACTTACGTTGAAAAGTGAGCGGATGAACTGWGGGTA GCGGAGAAATTCCAATCGAACTTGGAGATAGCTGGTTCTCT CCGAAATAGCTTTAGGGCTAGCCTCAAGTGATGATTATTGG AGGTAGAGCACTGTTTGGACGAGGGGCCYCTCTCGGGTTA CCGAATTCAGACAAACTCCGAATGCCAAT | 7 |
| Staphylococcus aureus | Immunoglobulin G binding protein A (spa) | GCTGATAACAATTTCAACAAAGAACAACAAAATGCTTTCTA TGAAATCTTGAATATGCCTAACTTAAACGAAGAACAACGC AATGGTTTCATCCAAAGCTTAAAAGATGACCCAAGCCAAA GTGCTAACCTATTGTCAGAAGCTAAAAAGTTAAATGAATCT CAAGCACCGAAAGCGGATAACAAATTCAACAAAGAACAAC AAAATGCTTTCTATGAAATCTTACATTTACCTAACTTAAAC GAAGAACAACGCAATGGTTTCATCCAAAGCCTAAAAGATG ACCCAAGCCAAAGCGCT | 8 |
| Staphylococcus capitis | Thermonuclease | TCAATTTATTAACCACGAAGGTCCATTTGGCGGTAAACAAT CAAATGAAAAAAATCTAAGCGCAGATTTAAAAGGAAAAGA TAAAGTTTATGTTGAACGTGTAGTAGATGGGGATACTTTTC TTGCTAAGAAAGATGGCGAGCGTATTAAAGTTAGAATGAT TGGTATGGATACACCAGAAACGGTTAAACAAATACGCCT GTTCAACCCTATGGTAAAGAAGCATCAAACTATAGTAAGA AAGAGTTAACACATAAGTATGTTTATTTAGAATACGATAAA GAAAAAAATGATAGATA | 9 |
| Staphylococcus epidermidis | Thermonuclease | CGATGATAGGAATACTTGTAATTATTTTCCAGTTTGTAAAC CATTCTGGACCGTTTAGTGATTCAGAATCTCAACATCAATC AGATAATTCCAATTTAAATGGTAAAGACAAAGTATATGTG AAACGAGTTGTAGATGGTGATACATTTGTTGCTCAAAAAAA TGGAGAGGAAATTAAAGTCAGATTAATTGGTGTAGATACG CCAGAGACTGTTAAGCCTAATACGCCAGTTCAACCATATGG TAAACAAGCATCTAATTATACGAAGAAGTATCTCACGCATC AAAATGTTTATTTAG | 10 |
| Staphylococcus lugdunensis | Thermonuclease | ACGCCTGAAACAGTGAAACCTAATACACCTGTACAGCCAT ACGGTAAAGAAGCATCGCATTTTAGTAAAAAGAACTTAAC CAATAAAGATGTTTATCTGGAATATGATAAAGAAAAAAAT GATCGCTATGGACGTGTTTTAGCATATGTTTGGCTGGATAA AGATACATTATTTAATGAGCTATTAGTAAAAGAAGGGTTAG CTAAAGAAAAATACTTTGCACCTAATGGAAAATATAGAGA CGTCTTTATCAAAGCACAAAACGAGGCGCAAAAGAAAAAA ATCAATCTTTGGAGTTAG | 11 |

TABLE 1-continued

| Target | Gene | Target Sequence | # |
|---|---|---|---|
| Streptococcus agalactiae | cAMP factor (cfb) | ATGAACGTTAAACATATGATGTATCTATCTGGAACTCTAGT GGCTGGTGCATTGTTATTTTCACCAGCTGTATTAGAAGTAC ATGCTGATCAAGTGACAACTCCACAAGTGGTAAATCATGTA AACAGTAATAATCAAGCCCAGCAAATGGCTCAAAAGCTTG ATCAAGATAGCATTCAGTTGAGAAATATCAAAGATAATGTT CAGGGAACAGATTATGAAAAAACGGTTAATGAGGCTATTA CTAGTGTTGAAAAATTAAAGACTTCATTGCGTGCCAACCCT GAGACAGTTTATGAT | 12 |
| Streptococcus anginosus group | 16S ribosomal subunit | AAAGGCAGTGGCTCAACCATTGTAGGCTTTGGAAACTGTTT AACTTGAGTGCAGAAGGGGAGAGTGGAATTCCATGTGTAG CGGTGAAATGCGTAGATATATGGAGGAACACCGGTGGCGA AAGCGGCTCTCTGGTCTGTAACTGACGCTGAGGCTCGAAAG CGTGGGGAGCGAACAGGATTAGATACCCTGGTAGTCCACG CCGTAAACGATGAGTGCTAGGTGTTAGGTCCTTTCCGGGAC TTAGTGCCG | 13 |
| Streptococcus mitts group | 16S ribosomal subunit | CTGACCGAGCAACGCCGCGTGAGTGAAGAAGGTTTTCGGA TCGTAAAGCTCTGTTGTAAGAGAAGAACGRGTGTGAGAGT GGAAAGTTCACACTGTGACGGTAWCTTACCAGAAAGGGAC GGCTAACTACGTGCCAGCAGCCGCGGTAATACGTAGGTCC CGAGCGTTRTCCGGATTTATTGGGCGTAAAGCGAGCGCAG GCGGTTAGATAAGTCTGAAGTTAAAGGCTGTGGCTTAACCA TAGTABGCTTTGGAAACTGTTTAACTTGAGTGCA | 14 |
| Streptococcus pneumoniae | Autolysin (lytA) | ACGTTGGGGCGGTTGGAATGCTGAGACCTATGCAGCGGT TGAACTGATTGAAAGCCATTCAACCAAAGAAGAGTTCATG ACGGACTACCGCCTTTATATCGAACTCTTACGCAATCTAGC AGATGAAGCAGGTTTGCCGAAAACGCTTGATACAGGGAGT TTAGCTGGAATTAAAACGCACGAGTATTGCACGAATAACC AACCAAACAACCACTCAGACCACGTTGACCCTTATCCATAT CTTGCTAAATGGGGCATTAGCCGTGAGCAGTTTAAGCATGA TATTGAGAACGGCTTGA | 15 |
| Streptococcus pyogenes | Sodium ATPase subunit C (ntpC) | TCAGTGTCAAAGAAAAAGAGTTATTGACTAAAGAGCAATT TGATAAGCTATTGCAGGCTCCCAATACAACAACCTTAGCTC GACTGTTGCACCAGTCAGTCTATCACCTAACTGTTGACGAT CTCAACGATTTGGATCGGCTAGAATCTATCTTAATGGCTGA GCTAACCAAGACCTATCGCTGGGCTTTTGCAGAAACCCCTC AACCTGACATAGTACAATTATTTACCTTGCGTTACACCTAT CATAATGTCAAAGTGTTGTTAAAAGCTAAAGCTAGTCAAGC AGATCTGAGTCACT | 16 |
| Tropheryma whipplei | Repeat region (TW625) | AGAGAGATGGGGTGCAGGACAGGGTTTGTTTTGTACTGCTT GTAACAGGATCTATTAGGAGAGATACATTTGTGTTAGTTGT TACACATACTTCTTGTGTATTTGTATTACTTACTCTTGTGTA TTTGGTAYTAGATGAAACAGATGTAGATGAAACAGATGAT AGGAGGGATAGRGCAGGAGGTGTCTGTCTGGCAAAGGCTG TTTCATATTGTAGGGATGATAGGAGGAGAAG | 17 |
| Acinetobacter calcoaceficus-baumanii | 16S-23S intergenic space | GGGTCACAAGTTCAAGTCTTGTCAGACCCACCATGACTTTG ACTGGTTGAAGTTATAGATAAAAGATACATGATTGATGATG TAAGCTGGGGACTTAGCTTAGTTGGTAGAGCGCCTGCTTTG CACGCAGGAGGTCAGGAGTTCGACTCTCCTAGTCTCCACCA GAACTTAAGATAAGTTCGGATTACAGAAATTAGTAAATAA AGATTAAGATCTTGGTTTATTAACTTCTGTGATTTCATTATC ACGGTAATTAGTGTGATCTGACGAAGACACATTAACTCATT AACAGATTGGCAA | 18 |
| Acinetobacter lwoffii | blaOXA-134 | GCCTGACAGCATGTAGCCTACCCGTTTCATCTCTCCCATCTC AAAGCATTTCGACTCAAGCGATTGCCAGCTTATTTGATCAG GCGCAAAGCTCTGGTGTTTTAGTGATTCAGCGTGATCAACA AGTACAGGTCTATGGCAATGATTTAAATCGTGCAAATACCG AATATGTTCCCGCCTCTACTTTTAAAATGCTCAATGCTCTGA TTGGCCTGCAACATGGCAAAGCCACAACCAATGAAATTTTT AAATGGGATGGCAAGAAACGCA | 19 |
| Enterobacter aerogenes | DNA gyrase subunit B (gyrB) | GCTGGCGGTAACCGGTGAAACCGAAAGCACCGGTACCATG GTGCGTTTCTGGCCAAGCCTGGAAACCTTTACCAACGTCAC TGAATTCGAATACGAAATCCTGGCGAAACGTCTGCGCGAG CTGTCGTTCCTCAACTCCGGGGTCTCTATCCGCCTGCGCGA TAAGCGCGACGGCAAAGAAGACCATTTCCACTACGAAGGC GGCATCAAGGCGTTTGTTGAGTATCTCAACAAGAACAAAA CGCCGATCCACCCGAATATCTTCTATTTCTCCACCGAAAAA GACGGTA | 20 |

TABLE 1-continued

| Target | Gene | Target Sequence | # |
|---|---|---|---|
| Escherichia coli | UDP-N-acetylmuramate-L-alanine ligase (murC) | CGTCATGGCATCGCCATTGCCGGAACGCACGGCAAAACGA CAACCACCGCGATGGTTTCCAGCATCTACGCAGAAGCGGG GCTCGACCCAACCTTCGTTAACGGCGGGCTGGTAAAAGCG GCGGGGGTTCATGCGCGTTTGGGGCATGGTCGGTACCTGAT TGCCGAAGCAGATGAGAGTGATGCATCGTTCCTGCATCTGC AACCGATGGTGGCGATTGTCACCAATATCGAAGCCGACCA CATGGATACCTACCAGGGCGACTTTGAGAATTTAAAACAG ACTTTTATTAATTTTCTG | 21 |
| Haemophilus influenzae | Phosphate ABC transporter permease (pstA) | TCAGGGTGGGCTGGAGCATTCGCATTAGCTTTATTGCTTAT TCCTATCGTGGTACGCACTACGGACAATATGTTATTACTTG TACCAAATAATTTACGTGAAGCAGCGGCAGCTCTTGGTTGC TCTCAATGGCAAGTTATTATGATGATTTGTTATCGAGCAGC TAAATCAGGGATTTTAACTGGCGTGCTATTAGCAGTTGCCC GAATTTCAGGAGAAACTGCACCGCTATTATTTACCGCTCTG TCTAATCAATTTCTATCTTGGAATATGAATGAACCTATCGC AAATTTACCTGTA | 22 |
| Klebsiella pneumoniae | DNA gyrase subunit B (gyrB) | AGTTTCTCGCCCAGGGCACAAATACGACGATATTCCGGCCC CATAATGAACTCGTTATCCAGCGGATAGTCGGTATCCACGC CGTGGGTACGTACGCGAATAACCGGCTCAAAATGCTGCAG TTCTTTGTTCTCGTGGAGATCGAATTTCCACTGGCTGCCGTG CTGTTCTTTCTCGTTCAGCTC | 23 |
| Morganella morgani | DNA gyrase subunit B (gyrB) | CATCCTGTACGGAGACTGAATTRTCATTGTGAATGGTCACA AYGATGTCTTTACAGTAACCGGCGAGGGCTTCGTCGATAGC GTTGTCAACAACCTCGAAGACCATGTGGTGTAAACCGGTTC CGTCATCGGTATCACCAATGTACATTCCCGGGCGTTTACGC ACCGCGTCCAGCCCTTTTAATACTTTGATACTTGAGGAGTC ATAGGTATTCGACAT | 24 |
| Proteus mirabilis | Acetate kenase (ackA) | TGTTAATACTATTCTGGCTGAGAAACCAGAACTTTCACAAC AAATCGCAGCAATTGGTCATCGTATTGTTCACGGTGGCGAG AAATTTACTAAATCTGTCGTCATTACTGACGAAGTCATCAA AGGTATTGAGGCGGCTATTCCATTTGCCCCATTACATAACC CAGCTCACCTTATTGGTATTGAAGAAGCGCGTAAAGCCTTC CCTCATTTAATTAATAAAATGGTGGCAGTATTTGACACTGC ATTCCACCAAACAATGCCAGAAGAAGCTTATCTGTATGCTC TGCCATACAGCTT | 25 |
| Pseudomonas aeruginosa | Gamma-glutamyl phosphate reductase (pro A) | ATGACCGAGTCCGTCCTCGACTATATGAGCCGCCTTGGCCG CGATGCCCGCGCCGCCTCGCGGTTGCTCGCGCGCGCCGCCA CCGCGCAGAAGAACCGCGCCCTGCTGGCCGCGGCCGATGC GCTGGACGCCGCCCGCGCGGAGTTGTCCCACGCCAACGAG CAGGACCTCGCCGCCGGCCGCGCCAATGGCCTGGAGCCGG CGATGCTGGACCGCCTGGCGCTGACCCCGGCGCGCATCGA CGACATGATCGAGGGCCTGCGCCAGGTCGCCACGCTGCCC GACCCGATCGGCGAGATC | 26 |
| Serratia marcescens | DNA gyrase subunit B (gyrB) | CCTCAAGTATCAAGGTATTAAAAGGGCTGGATGCGGTGCG CAAGCGCCCGGGCATGTATATCGGCGATACCGATGACGGC ACCGGTCTGCACCACATGGTATTCGAGGTTGTGGACAACGC TATCGACGAAGCGCTCGCGGGCCACTGTAGYGACATTCAG GTCACCATCCATGCYGACAACTCGGTATCGGTRCAGGATGA CGGCCGCGGCATTCCGACCGGCATTCACCCGGAAGAAGGG GTTTCAGCCGCAGAGGTCATCATGACCGTGCTGCACGCCGG CGGTAAATTCGACGACAACTCCTATAA | 27 |

Spirochetes

| Target | Gene | Target Sequence | # |
|---|---|---|---|
| Borrelia burgdorferi | Flagellin (flaB) | ACAGACGAAATTAATAGAATTGCTGATCAAGCTCAATATA ACCAAATGCACATGTTATCAAACAAATCTGCTTCTCAAAAT GTAAGAACAGCTGAAGAGCTTGGAATGCAGCCTGCAAAAA TTAACACACCAGCATCACTTTCAGGGTCTCAAGCGTCTTGG ACTTTAAGAGTTCATGTTGGAGCAAACCAAGATGAAGCTAT TGCTGTAAATATTTATGCAGCTAATGTTGCAAATCTTTTCTC TGGTGAGGGAGCTCAAACTGCTCAGGCTGCACCGGTTCAA GAGGGTGTTCAACAG | 28 |
| Treponema pallidum | Membrane antigen (tpp47) | CCCAGTTGCGGTTCCTCATGAATTAAAAGGGATTGCAAAGG AGAAGTTTCACTTCGTGGAAGACTCCCGCGTTACGGAGAAT ACCAACGGCCTTAAGACAATGCTCACTGAGGATAGTTTTTC TGCACGTAAGGTAAGCAGCATGGAGAGCCCGCACGACCTT GTGGTAGACACGGTGGGTACCGGTTACCACAGCCGTTTTGG TTCGGACGCAGAGGCTTCTGTGATGCTGAAAAGGGCTGAT GGCTCTGAGCTGTCGCACCGTGAGTTCATCGACTATGTGAT GAACTTCAACACGGT | 29 |

TABLE 1-continued

| Target | Gene | Target Sequence | # |
|---|---|---|---|
| Fungi | | | |
| *Aspergillus flavus* | Beta tubulin | TCTGACGGCAAGGATAGTTACAATGGCTCCTCCGATCTCCA GCTGGAGCGTATGAACGTCTACTTCAACGAGGTGCGTACCT CAAAATTTCAGCATCTATGAAAACGCTTTGCAACTCCTGAC CGCTTCTCCAGGCCAGCGGAAACAAGTATGTCCCTCGTGCC GTCCTCGTTGATCTTGAGCCTGGTACCATGGACGCCGTCCG TGCCGGTCCCTTCGGTCAGCTCTTCCGTCCCGACAACTTCGT TTTCGGCCAGTCCGGTGCTGGTAACAACTGGGCCAAGGGTC ACTACACTGAGG | 30 |
| *Aspergillus fumigatus* | Calmodulin | ATATTGAGGGTGTGCGCTGACACGAGATTTGACGTATAGG ACAAGGATGGTGATGGTTAGTGACCCTTTTTCCACTCCTCG AACTTCGGCTTCCATGCGATCATGTTCAAACGCCGACTCAC AATATCCGGAAATGACCCKTCAGTACTGATAATATCTATGT TTGACTATCAGGCCAGATCACCACCAAGGAATTGGGCACT GTAATGCGCTCTCTGGGCCAGAACCCTTCCGAGTCAGAGCT GCAAGATATGATCAACGAGGTGGATGCTGACAACAACGGC ACCATCGATTTCCCCG | 31 |
| *Aspergillus niger* | Calmodulin | CGGTGAATCAGGCCAGATCACCACCAAGGAGCTCGGCACT GTGATGCGCTCCCTTGGCCAGAACCCCTCCGAGTCTGAGCT TCAGGACATGATCAACGAGGTTGACGCTGACAACAACGGA ACGATCGACTTCCCCGGTATGTGTTAGATTTACGCCTGTAA GGCGGAAATGCGGGCTGGATTGTGATTGACTTTTGCCGCCA GAATTCCTTACCATGATGGCTCGTAAGATGAAGGACACCG ACTCCGAGGAGGAAATCCGCGAGGCTTTCAAG | 32 |
| *Candida albicans* | 28S ribosomal subunit | CTCTAAGTGGGTGGTAAATTCCATCTAAAGCTAAATATTGG CGAGAGACCGATAGCGAACAAGTACAGTGATGGAAAGATG AAAAGAACTTTGAAAAGAGAGTGAAAAAGTACGTGAAATT GTTGAAAGGGAAGGGCTTGAGATCAGACTTGGTATTTTGCA TGYTGCTCTCTCGGGGGCGGCCGCTGCGGTTTACCGGGCCA GCATCGGTTTGGAGCGGCAGGATAATGGCGGAGGAATGTG GCACGGCTTCTGCTGTGTGTTATAGCCTCTGACGATRCTGC CAGCCTAGACCGAGGACTGCGGTTTT | 33 |
| *Candida dubliniensis* | ITS1-5.8S-ITS2 intergenic space | AACTTACAACCAAATTTTTTATAAACTTGTCACGAGATTAT TTTTAATAGTCAAAACTTTCAACAACGGATCTCTTGGTTCTC GCATCGATGAAGAACGCAGCGAAATGCGATACGTAATATG AATTGCAGATATTCGTGAATCATCGAATCTTTGAACGCACA TTGCGCCCTCTGGTATTCCGGAGGGCATGCCTGTTTGAGCG TCGTTTCTCCCTCAAACCCCTAGGGTTTGGTGTTGAGCAAT ACGACTTGGGTTTGCTTGAAAGATGATAGTG | 34 |
| *Candida glabrata* | 28S ribosomal subunit | GTGTCAGTTCTTTGTAAAGGGTGCTCGAAGAGTCGAGTTGT TTGGGAATGCAGCTCTAAGTGGGTGGTAAATTCCATCYAAA GCTAAATACAGGCGAGAGACCGATAGCGAACAAGTACAGT GATGGAAAGATGAAAAGAACTTTGAAAAGAGAGTGAAAA AGTACGTGAAATTGTTGAAAGGGAAGGGCATTTGATCAGA CATGGTGTTTGCGC | 35 |
| *Candida tropicalis* | ITS1 intergenic space | GTTATAACTAAACCAAACTTTTTATTTACAGTCAAACTTGA TTTATTATTACAATAGTCAAAACTTTCAACAACGGATCTCT TGGTTCTCGCATCGATGAAGAACGCAGCGAAATGCGATAC GTAATATGAATTGCAGATATTCGTGAATCATCGAATCTTTG AACGCACATTGCGCCCTTTGGTATTCCAAAGGGCA | 36 |
| *Candida parapsiolosis* (sensulato) | 28S ribosomal subunit | CCCAGACCTATGTAAAGTTCCTTCGAAGAGTCGAGTTGTTT GGGAATGCAGCTYAAGTGGGTGGTAAATTCCATCTAAAG CTAAATATTGGCGAGAGACCGATAGCGAACAAGTMCAGTG ATGGAAAGATGAAAAGAACTTTGAAAAGAGAGTGAAAAA GTACGTGAAATTGTTGAAAGGGAAGGGCTTGAGATCAGAC TTGGTATTTTGTATGTTACTCYTCGGGGGTGGCCTCTACAG TTTACCGGGCCAGCATCAGTTTGRGCGGTAGGABAAKTGCA AAGAAATGTGGCACTGC | 37 |
| *Fusarium spp.* | 28S ribosomal subunit | CCGAGTTGTAATTTGTAGAGGATRCTTTTGRYRMGGTGCCT TCCGAGTWCCCTGGAACGGGACGCCATAGAGGGTGAGAGC CCCGTCTGGTTGGAYRCCRADYCTCTGTAAAGYTCCTTCRA CGAGTCGAGTAGTTTGGGAATGCTGCTCTAAATGGGAGGT ATATGTCTTCTAAAGCTAAATACYGGCCAGAGACCGATAG CGCACAAGTAGAGTGATCGAAAGATGAAAAGMACTTTGAA AAGAGRGTTAAAMAGYACGTGAAATTGTTGAAA | 38 |

TABLE 1-continued

| Target | Gene | Target Sequence | # |
|---|---|---|---|
| *Fusarium solani* | Calmodulin (cmdA) | GCCGTTGTTGTCGGCGTCGACCTCGTTGATCATGTCCTGAA GCTCAGACTCGGAGGGGTTCTGGCCGAGGGAGCGCATGAC GGTGCCCAGCTCCTTGGTGGTGATCTGGCCTAGAGCGAAAC GTTTAGTTTACCGTCTCGAAACGATTCGCATCGACTGAAGA GCAGTGTGCGCATAGAGGTTCGATGCATCATGTAATTCGGA AAAGGAATCGGGCTGAGGCCGACGAGGGGCTTTGCGAGCA GGAGGGAGAATCACTCACCATCGCCATCCTTGTCCTATGCA AGAGGTTAGCGACAG | 39 |
| Viruses | | | |
| Cytomegalovirus | Immediate-early gene (UL123) | TCTCAGACACTGGCTCAGACTTGACAGACACAGTGTCCTCC CGCTCCTCCTGAGCACCCTCCTCCTGTTCCTCATCACTCTGT TCACTTTCTTCCTGATCACTGTTCTCAGCCACAATTACTGAG GACAGAGGGATAGTCGCGGGTACAGGGGACTCTGGAGGTG ACACCAGAGAATCAGAGGAGCTGGCACCAGCGGTGGCCAA AGTGTAGGCTACAATAGCCTCTTCCTCATCTGACTCCTCGG CGATGGCCCGTAGGTCATCCACACTAGGAGAGCAGACTCT CAAAGGATCGGCCC | 40 |
| Epstein-barr virus | DNA polymerase (BALF5) | GACATAGAGGGGGTTGAGGTCTACGAGTTCCCATCGGAGC TGGACATGCTCTACGCCTTCTTCCAGCTCATCAGAGACCTC AGCGTGGAGATTGTGACCGGCTACAACGTGGCCAACTTTG ACTGGCCCTACATTCTGGACAGAGCCAGGCACATCTACAGC ATCAACCCAGCCTCTCTGGGCAAAATTAGGGCTGGGGGCG TCTGCGAGGTCAGGCGACCCCATGATGCGGGCAAGGGCTT CTTGCGGGCCAACACCAAGGTCCGCATCACCGGCCTCATCC CCATCGACATGTACGCC | 41 |
| Herpes simplex 1 | DNA polymerase catalytic subunit (UL30) | AGCTCTCGAGCTACAAGCTCAACGCCGTGGCCGAAGCCGT CCTGAAGGACAAGAAGAAGGACCTGAGCTATCGCGACATC CCCGCCTACTACGCCACCGGGCCCGCGCAACGCGGGGTGA TCGGCGAGTACTGCATACAGGATTCCCTGCTGGTGGGCCAG CTGTTTTTTAAGTTTTTGCCCCATCTGGAGCTCTCGGCCGTC GCGCGCTTGGCGGGTATTAACATCACCCGCCACCATCTACGA CGGCCAGCAGATCCGCGTCTTTACGTGCCTGCTGCGCCTGG CCGACCAGAAGGGCT | 42 |
| Herpes simples 2 | DNA polymerase catalytic subunit (UL30) | GGCGGCGTCTGGGTTTTTTGCCCCCCACAACCCCCGGGGAG CCACCCAGACGGCACCGCCGCCTTGCCGCCGGCAGAACTTC TACAACCCCCACCTCGCTCAGACCGGAACGCAGCCAAAGG CCCTCGGGCCGGCTCAGCGCCATACGTACTACAGCGAGTGC GACGAATTTCGATTTATCGCCCCGCGTTCGCTGGACGAGGA CGCCCCGCGGAGCAGCGCACCGGGGTCCACGACGGCCGC CTCCGGCGCGCCCCTAAGGTGTACTGCGGGGGGGACGAGC GCGACGTCCTCCGCGT | 43 |
| Human herpes virus 6 | Glycoprotein (U22) | AAGTGGAACTGCTTGGTGGCGGATGGCTAGTGTGCCTATTA ATGCTTATTTCGAAAGAGATATAGCCTTTTTATTTAACCCTC GATGCGTTATCGAGACTGCCCTGGGGTCTAAGATATTATGT CGATACAATAAAAATATTGGTGTTGTGTTTGTGGACAATGA TACTACGTGTAATGTTTCCTTTCCGAGCGGTGTGCAGTTAC AATTACTAAATCAATCGGTGATGGAGTCAATTAGAACTAA AACGTATGTAGTGGATTACGCTAGGAAAACTACAGAGAGA GGTGATTGCTTCAT | 44 |
| Varicella zoster | Regulatory protein (ORF63) | GGATACGTCGCGGGGCCCCGGCGCGTTTTGTACTCCGGGTT GGGAGATCCACCCGGCCAGGCTCGTTGAGGACATCAACCG TGTTTTTTTATGTATTGCACAGTCGTCGGGACGCGTCACGC GAGATTCACGAAGATTGCGGCGCATATGCCTCGACTTTTAT CTAATGGGTCGCACCAGACAGCGTCCCACGTTAGCGTGCTG GGAGGAATTGTTACAGCTTCAACCCACCCAGACGCAGTGCT TACGCGCTACTTTAATGGAAGTGTCCCATCGACCCCCTCGG GGGGAAGACGGGTT | 45 |
| Parasite | | | |
| *Toxoplasma gondii* | Glycerol-3-phosphate dehydrogenase | TTTGCATAGGTTGCAGTCACTGACGAGCTCCCCTCTGCTGG CGAAAAGTGAAATTCATGAGTATCTGTGCAACTTTGGTGTA TTCGCAGATTGGTCGCCTGCAATCGATAGTTGACCACGAAC GCTTTAAAGAACAGGAGAAGAAGATCGTGAAAGAATACGA GAAGAGGTACACAGAGATAGAAGTCGCTGCGGAGACAGCG AAGACTGCGGATGACTTCACTCCCGTCGCACCAGCAGCAG AGGAGTGCCGGGCAAGAAAATGAGATGCCTAGAGGAGAC ACAGCGTGTTATGAACAAATCTATTGAGGTTTCGCGAAGAG GAGGGAACATATTATATACAGAAGAAGAACAAGAGACGTG CCGCATGTCGCTAAGCCATCGGAAGGGATGCTCAGAAAAT | 46 |

TABLE 1-continued

| Target | Gene | Target Sequence | # |
|---|---|---|---|
| | | GGCACAGTATCACATTACAGTTCCGTTGATTCGTCTGATGG<br>TGACGAAAGGGGAAGAATAGTTGTCGCACCAAAACTSGCT<br>AGTTGTTAYTTTGAAGAAGACGAGAGATGGAGTGAACCAC<br>CAAAAATCGGAGAAAATCGATGGTGTCACGTTTTTTGTCAG<br>ACTTCACTTTGTGCAGAAGCATTGCCCGTCCAAACTGCAAC<br>AACTGCTCTAGCGTGTTCGTCTCCATTCCGTACAGTCTTCAA<br>AAATACAAAAGAGAACATTCCAGCAACTTCTRCCTTTGTTC<br>TTTTAGCCTCAATAGCAGGATGACGCCTCCCTCCTATCTTTC<br>AGCCAACCCAGCAAACACCGACGAACTCTCTGTAGAGTAA<br>CAA | |
| Staphylococcus epidermidisica locus | icaA-D | TACAGTTGCCTTATTTATTGACAGTCGCTACGAAAAGAAAA<br>ATATAGTTGGCCTGATATTTTTAAGTTGGTATCCAACGTTAT<br>ACTGGGTTATCAATGCCGCAGTTGTCATTATGGCATTTCCT<br>AAAGCATTAAAAAGAAAGAAAGGTGGCTATGCTACATGGT<br>CAAGCCCAGACAGAGGCAATATCCAACGGTAACCTCTTATT<br>TAAATATAGTTAGGGAGAGCTTATTTATTACTATATCCGGA<br>GTATTTTGGATGTATTGTATCGTTGTGATGATTGTTTATATA<br>GGAACTCTTAT | 47 |
| Staphylococci mec A | mecA | TGAAAAATGATTATGGCTCAGGTACTGCTATCCACCCTCAA<br>ACAGGTGAATTATTAGCACTTGTAAGCACACCTTCATATGA<br>CGTCTATCCATTTATGTATGGCATGAGTAACGAAGAATATA<br>ATAAATTAACCGAAGATAAAAAAGAACCTCTGCTCAACAA<br>GTTCCAGATTACAACTTCACCAGGTTCAACTCAAAAAATAT<br>TAACAGCAATGATTGGGTTAAATAACAAAACATTAGACGA<br>TAAAACAAGTTATAAAATCGATGGTAAAGGTTGGCAAAAA<br>GATAAATCTTGGGGTG | 48 |

, SEQ ID NO:

Multiplex-Targeted Enrichment

Because of the low pathogen biomass in ocular specimens, analytical sensitivity of an assay is critical for its clinical applications. To deal with that issue, we performed a multiplex-targeted enrichment step before detecting species-specific DNA segments with barcoded probes. Primers flanking the targeted genomic regions that bind to the specific probes were designed (described above). A 10-µl polymerase chain reaction is set up using 5 µl of 2x TaqMan PCR master mix, 1 µl of the primer mixture at 0.5 nM per oligonucleotide, 2.5 µl of purified DNA and sterile water to complete to the final volume. PCR was performed under the following conditions: 94° C. denaturation for 5 minutes followed by 20 cycles of 15 seconds at 94° C. and 4 minutes at 60° C. This number of cycles was found to improve sensitivity while maintain a low level of background noise.

DNA Detection

DNA from control organisms used for analytical validation and from clinical specimens were extracted and purified using the DNeasy blood and tissue kit (Qiagen), following the tissue protocol. Purified DNA was eluted from the silica membrane in 50 µL EB buffer and used as input for the multiplex-targeted enrichment step described above. Enriched samples were than mixed with a cocktail of 96 probes (2 50 mer probes per each of the 48 targets), containing one capture probe that secures the target of interest to the analysis matrix, and a second 50 mer that attaches a unique color-coded barcode for that pathogen or resistance/virulence gene. The hybridization was performed at 67° C. for 16 h and the resulting products analyzed in the Nanostring nCounter Digital Analyzer.

Analytical Specificity.

The analytical specificity of the panel has been tested for a subset of organisms. Purified genomic DNA from herpes virus 1 strain MacIntyre (VR-529DQ), herpes virus 2 strain MS (VR-540DQ), varicella zoster virus (VZV) strain Ellen (VR-1367DQ), cytomegalovirus (CMV) strain AD169 (VR-538DQ), Staphylococcus aureus (Strain MRSA USA300), Staphylococcus epidermidis (ATCC35984), Staphylococcus lugdunensis (clinical isolate), Staphylococcus capitis (clinical isolate), Streptococcus pyogenes (ATCC19615), Streptococcus agalactiae (ATCC13813), Enterococcus faecalis (ATCC700802) and Pseudomonas aeruginosa (ATCC27853) were used for probe specificity validation.

Analytical Sensitivity.

Analytical sensitivity was evaluated for a constricted number of targets present in the panel. Preliminary testing were performed using purified genomic DNA from one Gram-positive (S. aureus USA300 strain) and one Gram-negative pathogen (P. aeruginosa ATCC27583) and Cytomegalovirus (strain AD169; VR-538DQ), serially diluted (10-fold) from 1 pg/µl to 1 fg/µl.

Validation with Ocular Specimens.

Protocols for collection of discarded intraocular specimens were approved by the Massachusetts Eye and Ear Institutional Review Board. Samples were obtained either by anterior paracentesis (aqueous samples), posterior chamber paracentesis (undiluted vitreous samples), or during pars plana vitrectomy (both undiluted vitreous and diluted vitreous washing samples). Following collection, all specimens were immediately transported to the laboratory and stored at −20° C.

Example 1

Figure 2:
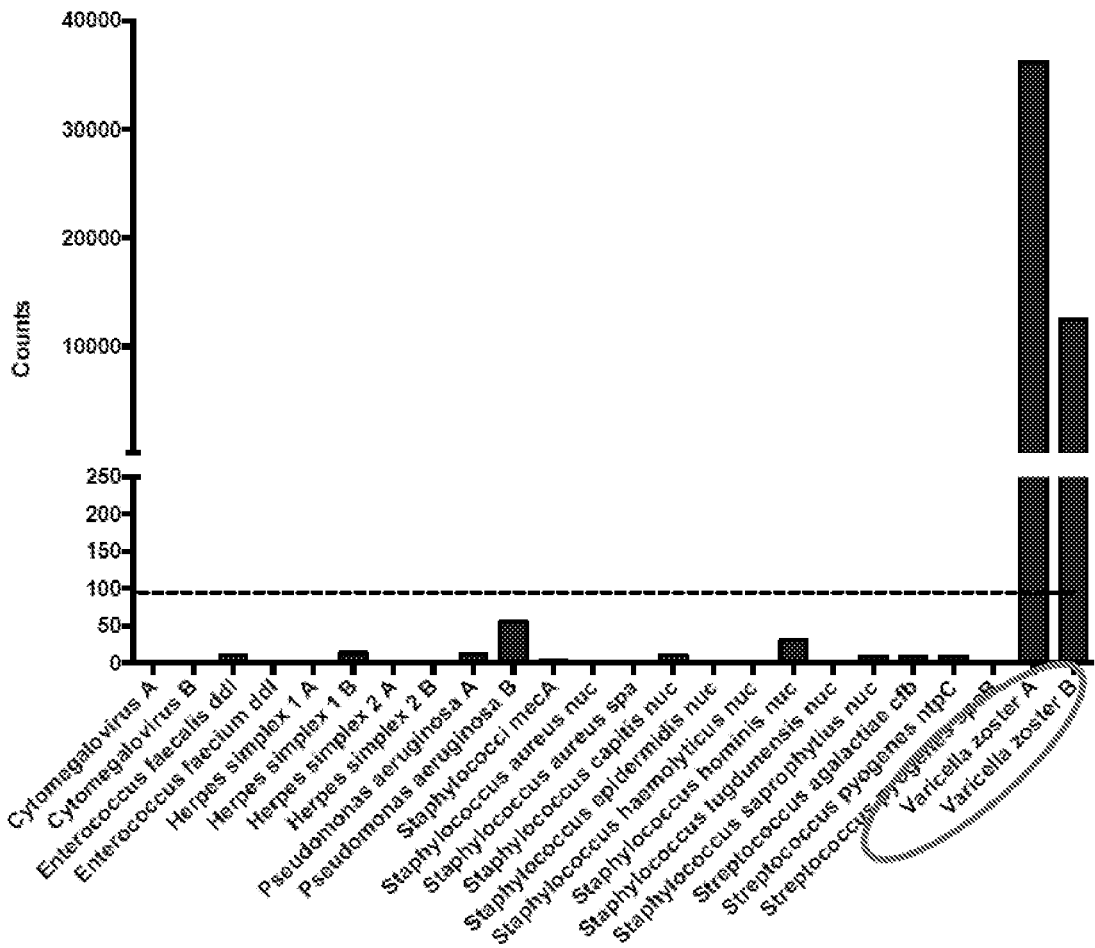
FIG. 2 is a bar graph showing detection of VZV in a sample spiked with control VZV DNA.

The probes and primers have been shown to be highly specific. We tested the analytical specificity of this panel using a collection of control DNA from bacteria (8 different species plus 1 antimicrobial resistant gene) and herpesviruses (n=4) (Table 2). All the probes and oligonucleotides tested demonstrated excellent target specificity, with no cross-reactivity detected. Exemplary results are shown in FIG. 2.

TABLE 2

List of targets tested for analytical specificity

| Organism | Control Isolate |
|---|---|
| Bacteria | |
| Staphylococcus aureus | MRSA USA300 strain |
| Staphylococcus epidermidis | S. epidermidis ATCC35984 |
| Staphylococcus lugdunensis | Clinical isolate (identified by MicroScan) |
| Staphylococcus capitis | Clinical isolate (identified by MicroScan) |
| Streptococcus pyogenes | ATCC19615 |
| Streptococcus agalactiae | ATCC13813 |
| Enterococcus faecalis | ATCC 700802, V583 strain |
| Pseudomonas aeruginosa | P. aeruginosa ATCC27583 |
| Virus | |
| Cytomegalovirus | CMV-AD169 |
| Varicella zoster | VZV-Rod |
| Herpes simplex 1 | HSV-1 |
| Herpes simples 2 | HSV-2 |
| Resistance Markers | |
| mecA | MRSA USA300 strain |

Figure 3:
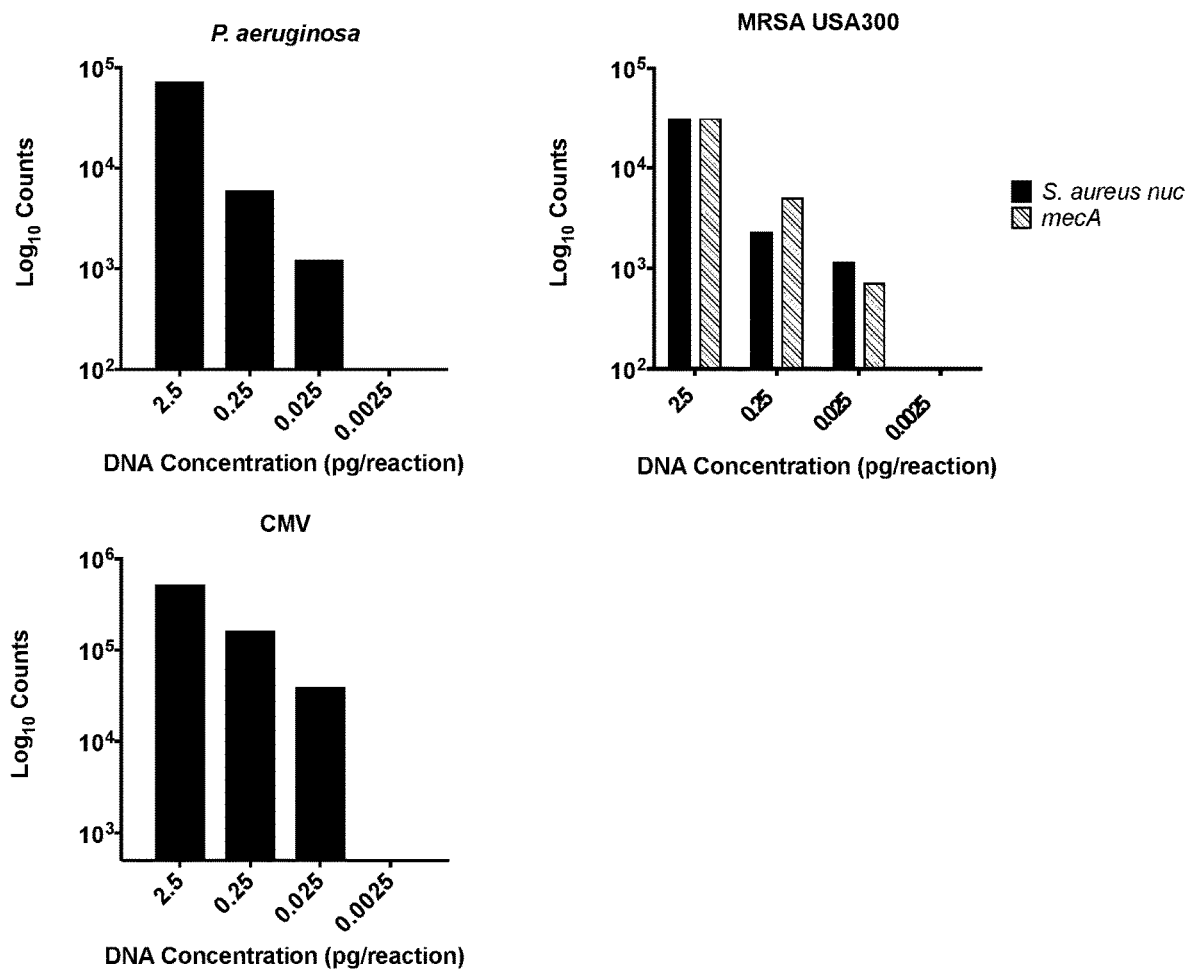
FIG. 3 is a trio of bar graphs showing the analytical sensitivity of detection tested with common organisms causing eye infections. Serial 10-fold dilutions ranging from 2.5 pg/reaction to 2.5 fg/reaction for a Gram-positive (MRSA USA300), a Gram-negative (*P. aeruginosa*) organism, and cytomegalovirus (CMV) were tested. The limit of detection for the 3 organisms was 25 femtograms of DNA per reaction.

The panel we tested could detect minute amounts of DNA. Serial 10-fold dilutions of DNA ranging from 2.5 pg/reaction to 2.5 fg/reaction were tested in order to determine the limits of detection (LoD). We used purified control DNA from *P. aeruginosa* (ATCC27853), methicillin-resistant *S. aureus* (MRSA strain USA300) and Cytomegalovirus (CMV), organisms that are commonly associated with eye infections. As low as 25 femtograms of DNA per reaction was detected for the 3 pathogens tested (FIG. 3).

Detection and identification were shown to be possible directly from the primary eye sample. To challenge this diagnostic panel with clinical eye specimens, we performed a small pilot study testing 3 different intraocular fluids (aqueous, vitreous and vitreous wash) collected from patients with CMV and VZV retinitis that were previously confirmed by real-time PCR. The NanoString-based multiplex panel was capable to correctly identify the causative agent from all the intraocular fluid matrices tested (Table 3). The detection was very robust, with counts for the correct pathogen 3 to 4 logs higher than the reaction noise.

TABLE 3

Specific identification and robust detection of herpesviruses from 3 intraocular specimens

| Clinical Diagnosis | Specimen | Nanostring Detection | | | Real Time PCR Result |
|---|---|---|---|---|---|
| | | Probe Identity | Probe A count | Probe B count | |
| CMV Retinitis | Aqueous humor | CMV | $5 \times 10^5$ | $7 \times 10^5$ | CMV |
| CMV Retinitis | Vitreous wash | CMV | $1 \times 10^5$ | $1.5 \times 10^5$ | CMV |
| Acute Retinal Necrosis | Vitreous tap | VZV | $7 \times 10^5$ | $1 \times 10^6$ | VZV |

REFERENCES

1. Bispo P J, de Melo G B, Hofling-Lima A L, Pignatari A C. Detection and gram discrimination of bacterial pathogens from aqueous and vitreous humor using real-time PCR assays. *Invest Ophthalmol Vis Sci* 2011; 52:873-881.
2. Dabil H, Boley M L, Schmitz T M, Van Gelder R N. Validation of a diagnostic multiplex polymerase chain reaction assay for infectious posterior uveitis. *Arch Ophthalmol* 2001; 119:1315-1322.
3. De Groot-Mijnes J D, Rothova A, Van Loon A M, et al. Polymerase chain reaction and Goldmann-Witmer coefficient analysis are complimentary for the diagnosis of infectious uveitis. *Am J Ophthalmol* 2006; 141:313-318.
4. Harper T W, Miller D, Schiffman J C, Davis J L. Polymerase chain reaction analysis of aqueous and vitreous specimens in the diagnosis of posterior segment infectious uveitis. *Am J Ophthalmol* 2009; 147:140-147 e142.
5. Sugita S, Ogawa M, Shimizu N, et al. Use of a comprehensive polymerase chain reaction system for diagnosis of ocular infectious diseases. *Ophthalmology* 2013; 120:1761-1768.
6. Sugita S, Shimizu N, Watanabe K, et al. Use of multiplex PCR and real-time PCR to detect human herpes virus genome in ocular fluids of patients with uveitis. *Br J Ophthalmol* 2008; 92:928-932.
7. Taravati P, Lam D, Van Gelder R N. Role of molecular diagnostics in ocular microbiology. *Curr Ophthalmol Rep* 2013; 1.
8. Barczak A K, Gomez J E, Kaufmann B B, Hinson E R, Cosimi L, Borowsky M L, Onderdonk A B, Stanley S A, Kaur D, Bryant K F, Knipe D M, Sloutsky A, Hung D T. RNA signatures allow rapid identification of pathogens and antibiotic susceptibilities. Proc Natl Acad Sci USA. 2012 Apr. 17; 109(16):6217-22.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method comprising:
providing a sample comprising intraocular fluid;
purifying genomic DNA from the sample;
performing PCR by contacting the sample with a plurality of sets of primers to amplify each of at least 40 of the target sequences SEQ ID NOs: 1-48, or its complement, in the genomic DNA; and
contacting the amplified DNA with a plurality of detectable probes that bind to each of the at least 40 of the target sequences, or its complement, wherein the plurality comprises at least 2 detectable probes that bind to each of the at least 40 of the target sequences, or its complement.

2. The method of claim 1, further comprising determining identity of the probes bound to the amplified DNA and determining sequence of the amplified DNA based on the identity of the bound probes, wherein determining the identity comprises using high resolution melting analysis.

3. The method of claim 1, wherein the sample comprises aqueous humor, vitreous humor, or vitreous wash.

4. A method of selecting a treatment and treating a subject who has uveitis, the method comprising:
providing a sample from an eye of the subject comprising, or suspected of comprising, a pathogen;
optionally purifying genomic DNA from the pathogen;
performing PCR by contacting the sample with a plurality of sets of primers to amplify each of at least 40, of the target sequences SEQ ID NOs: 1-48, or its complement, in genomic DNA from the pathogen; and
contacting the amplified DNA with a plurality of detectable probes that bind to each of the at least 40 of the target sequences, or its complement, wherein the plurality comprises at least 2 detectable probes that bind to each of the at least 40 of the target sequences, or its complement;
detecting binding of the at least 2 probes to the amplified DNA;
determining identity of the probes bound to the amplified DNA and determining sequence of the amplified DNA based on the identity of the bound probes;
correlating the sequence of the amplified DNA to a pathogen, thereby identifying the pathogen; and
selecting and administering to the subject a treatment for the identified pathogen, wherein the treatment is an antiviral for a viral pathogen, an antifungal for a fungal pathogen, an antibacterial for a bacterial pathogen, or anti-parasitic treatment for a parasitic pathogen.

5. The method of claim 4, wherein determining the identity comprises using high resolution melting analysis.

6. The method of claim 4, wherein the sample comprises aqueous humor, vitreous humor, or vitreous wash.

7. A kit comprising:
a plurality of sets of primers that amplify each of at least 40 of the target sequences SEQ ID NOs:1-48, or its complement;
a plurality of probes that bind to each of the at least 40 of the target sequences, or its complement, wherein each of the probes comprises a barcode sequence; and
optionally one or more reagents for performing a multiplexed gene analysis method.

8. The kit of claim 7, wherein the kit comprises one or more reagents for performing a multiplexed gene analysis method, and wherein the multiplexed gene analysis method is a hybridization based digital barcode quantification assay.

9. The kit of claim 7, wherein the plurality of probes comprises at least 2 probes that bind to each of the at least 40 of the target sequences.

* * * * *

SEQUENCE LISTING

<160> NUMBER OF SEQ ID NOS: 48

<210> SEQ ID NO 1
<211> LENGTH: 281
<212> TYPE: DNA
<213> ORGANISM: Bacillus cereus

<400> SEQUENCE: 1

```
gaatgcaaag agcgtgatgt gacgtatgca gcaccacttc gtgtaaaagt gcgtctaatc     60
aacaaggaaa ctggtgaagt aaaagaacaa gatgtgttca tgggagattt cccactcatg    120
acagagactg gaacattcgt aattaacggt gcagaacgtg ttatcgtttc ccagttagtt    180
cgctctccaa gcgtatacta tagtggcaaa gtggataaaa acggaaaacg tggtttttact   240
gctactgtaa ttccaaaccg cggagcttgg ttagagtatg a                         281
```

<210> SEQ ID NO 2
<211> LENGTH: 255
<212> TYPE: DNA
<213> ORGANISM: Bacillus subtilis

<400> SEQUENCE: 2

```
cccaggcgac tgtttagcaa aaacacaggt ctctgcgaag ccgtaaggcg aagtataggg     60
gctgacgcct gcccggtgct ggaaggttaa gaggagcgct tagcgtaagc gaaggtgcga    120
attgaagccc cagtaaacgg cggccgtaac tataacggtc ctaaggtagc gaaattcctt    180
gtcgggtaag ttccgacccg cacgaaaggc gcaacgatct gggcactgtc tcaacgagag    240
actcggtgaa attat                                                     255
```

<210> SEQ ID NO 3
<211> LENGTH: 300
<212> TYPE: DNA
<213> ORGANISM: Entero coccus faecalis

<400> SEQUENCE: 3

```
tagaaagcga catctttcac cacttcacca ggtaaagtcg tacggacatc ttcatttcct     60
aaaatggcta cttcaatttc acgtgcttcg atcccttgtt caacaattgc tcgggcatca    120
taacggaaag cttcttccaa tgcttcttgc aattcttcac gattttccac tttgctaatt    180
ccgacactag aacccatatt ggcaggttta acaaagaccg gataaattaa agaaccttca    240
catttttcaa agacttcttt tggatttcct ttccagtcac ttcttaaaac tggcacgaat    300
```

<210> SEQ ID NO 4
<211> LENGTH: 300
<212> TYPE: DNA
<213> ORGANISM: Entero coccus faecium

<400> SEQUENCE: 4

```
ttattcattt ttttcaaaaa aagattgacg ctgatggtat cgattcattc ctaactggat     60
cagttcttca atcaaatcac cgtatttcaa gcccatattt tcccataaga gtgggtacat    120
actgaactcc gtaaatcctg gcatagagtt taattcattc aggaataatt cattttttatt   180
tgtcaaaaag aaatcgcacc ggctcaatcc gcttccacct aacatcgtgt aagctaactt    240
cgcgtactct tgcgcttttt gataaacttc ttctggcact tcggctggaa tctgcatttc    300
```

<210> SEQ ID NO 5
<211> LENGTH: 300
<212> TYPE: DNA
<213> ORGANISM: Myco bacterium tuberculosis

<400> SEQUENCE: 5

```
ccgtggtgct caaggtctac cagaacgccg gcggcacgca cccaacgacc acgtacaagg     60
ccttcgattg ggaccaggcc tatcgcaagc caatcaccta tgacacgctg tggcaggctg    120
```

```
acaccgatcc gctgccagtc gtcttcccca ttgtgcaagg tgaactgagc aagcagaccg    180
gacaacaggt atcgatagcg ccgaatgccg gcttggaccc ggtgaattat cagaacttcg    240
cagtcacgaa cgacggggtg attttcttct tcaacccggg ggagttgctg cccgaagcag    300
```

<210> SEQ ID NO 6
<211> LENGTH: 300
<212> TYPE: DNA
<213> ORGANISM: Propioni-bacterium acnes

<400> SEQUENCE: 6

```
atgaagatca acgcacgatt cgccgtcatg gccgcgagtg tggccgtcct gatggctgcc     60
gcgccgattg cgcaggctgc tacttcgccg ggggatatcc atccctggt ccaggcagcc    120 cacagccccg acggtattcc cggtaacggc gtcgggccgg aattccatac gtcgtcgatg    180
gcgcgttcct acagcgagaa gcacctgggc gtggcgccgc ggggtgtgaa cgacttctcc    240
tgcaaggtca gcccggcga ccgaccggtc atcctgattc ccggtactgg cggcaatgcg    300
```

<210> SEQ ID NO 7
<211> LENGTH: 271
<212> TYPE: DNA
<213> ORGANISM: Staphylo-coccus spp.

<400> SEQUENCE: 7

```
agtatttggt cgtagacccg aaaccaggtg atctacccwt ggtcaggttg aagttcaggt     60
aacactgaat ggaggaccga accgacttac gttgaaaagt gagcggatga actgwgggta    120
gcggagaaat tccaatcgaa cttggagata gctggttctc tccgaaatag ctttagggct    180
agcctcaagt gatgattatt ggaggtagag cactgtttgg acgaggggcc yctctcgggt    240
taccgaattc agacaaactc cgaatgccaa t                                   271
```

<210> SEQ ID NO 8
<211> LENGTH: 300
<212> TYPE: DNA
<213> ORGANISM: Staphylo-coccus aureus

<400> SEQUENCE: 8

```
gctgataaca atttcaacaa agaacaacaa aatgctttct atgaaatctt gaatatgcct     60
aacttaaacg aagaacaacg caatggtttc atccaaagct aaagatgaa cccaagccaa    120 agtgctaacc tattgtcaga agctaaaaag ttaaatgaat ctcaagcacc gaaagcggat    180
aacaaattca caaagaaca caaaatgct ttctatgaaa tcttacattt acctaactta    240
aacgaagaac aacgcaatgg tttcatccaa agcctaaaag atgacccaag ccaaagcgct    300
```

<210> SEQ ID NO 9
<211> LENGTH: 300
<212> TYPE: DNA
<213> ORGANISM: Staphylo-coccus capitis

<400> SEQUENCE: 9

```
tcaatttatt aaccacgaag gtccatttgg cggtaaacaa tcaaatgaaa aaaatctaag     60
cgcagattta aaaggaaaag ataaagttta tgttgaacgt gtagtagatg gggatacttt    120
tcttgctaag aaagatggcg agcgtattaa agttagaatg attggtatgg atacaccaga    180
aacggttaaa ccaaatacgc ctgttcaacc ctatggtaaa gaagcatcaa actatagtaa    240
gaaagagtta acacataagt atgtttattt agaatacgat aaagaaaaaa atgatagata    300
```

<210> SEQ ID NO 10
<211> LENGTH: 300
<212> TYPE: DNA
<213> ORGANISM: Staphylo-coccus epidermidis

<400> SEQUENCE: 10

| | | | | | |
|---|---|---|---|---|---|
| cgatgatagg | aatacttgta | attattttcc | agtttgtaaa | ccattctgga | ccgtttagtg | 60 |
| attcagaatc | tcaacatcaa | tcagataatt | ccaatttaaa | tggtaaagac | aaagtatatg | 120 |
| tgaaacgagt | tgtagatggt | gatacatttg | ttgctcaaaa | aatggagag | gaaattaaag | 180 |
| tcagattaat | tggtgtagat | acgccagaga | ctgttaagcc | taatacgcca | gttcaaccat | 240 |
| atggtaaaca | agcatctaat | tatacgaaga | agtatctcac | gcatcaaaat | gtttatttag | 300 |

<210> SEQ ID NO 11
<211> LENGTH: 300
<212> TYPE: DNA
<213> ORGANISM: Staphylo-coccus lugdunensis

<400> SEQUENCE: 11

| | | | | | |
|---|---|---|---|---|---|
| acgcctgaaa | cagtgaaacc | taatacacct | gtacagccat | acggtaaaga | agcatcgcat | 60 |
| tttagtaaaa | agaacttaac | caataaagat | gtttatctgg | aatatgataa | agaaaaaaat | 120 |
| gatcgctatg | gacgtgtttt | agcatatgtt | tggctggata | agatacatt | atttaatgag | 180 |
| ctattagtaa | aagaagggtt | agctaaagaa | aaatactttg | cacctaatgg | aaaatataga | 240 |
| gacgtctta | tcaaagcaca | aaacgaggcg | caaaagaaaa | aaatcaatct | ttggagttag | 300 |

<210> SEQ ID NO 12
<211> LENGTH: 300
<212> TYPE: DNA
<213> ORGANISM: Strepto-coccus agalactiae

<400> SEQUENCE: 12

| | | | | | |
|---|---|---|---|---|---|
| atgaacgtta | aacatatgat | gtatctatct | ggaactctag | tggctggtgc | attgttatt | 60 |
| tcaccagctg | tattagaagt | acatgctgat | caagtgacaa | ctccacaagt | ggtaaatcat | 120 |
| gtaaacagta | ataatcaagc | ccagcaaatg | gctcaaaagc | ttgatcaaga | tagcattcag | 180 |
| ttgagaaata | tcaaagataa | tgttcaggga | acagattatg | aaaaaacggt | taatgaggct | 240 |
| attactagtg | ttgaaaaatt | aaagacttca | ttgcgtgcca | accctgagac | agtttatgat | 300 |

<210> SEQ ID NO 13
<211> LENGTH: 252
<212> TYPE: DNA
<213> ORGANISM: Strepto-coccus anginosus

<400> SEQUENCE: 13

| | | | | | |
|---|---|---|---|---|---|
| aaaggcagtg | gctcaaccat | tgtaggcttt | ggaaactgtt | taacttgagt | gcagaagggg | 60 |
| agagtggaat | tccatgtgta | gcggtgaaat | gcgtagatat | atggaggaac | accggtggcg | 120 |
| aaagcggctc | tctggtctgt | aactgacgct | gaggctcgaa | agcgtgggga | gcaacagga | 180 |
| ttagatacccc | tggtagtcca | cgccgtaaac | gatgagtgct | aggtgttagg | tcctttccgg | 240 |
| gacttagtgc | cg | | | | | 252 |

<210> SEQ ID NO 14
<211> LENGTH: 275
<212> TYPE: DNA
<213> ORGANISM: Strepto-coccus mitis

<400> SEQUENCE: 14

```
ctgaccgagc aacgccgcgt gagtgaagaa ggttttcgga tcgtaaagct ctgttgtaag      60
agaagaacgr gtgtgagagt ggaaagttca cactgtgacg gtawcttacc agaaagggac     120
ggctaactac gtgccagcag ccgcggtaat acgtaggtcc cgagcgttrt ccggatttat     180
tgggcgtaaa gcgagcgcag gcggttagat aagtctgaag ttaaaggctg tggcttaacc     240
atagtabgct ttggaaactg tttaacttga gtgca                                275
```

<210> SEQ ID NO 15
<211> LENGTH: 300
<212> TYPE: DNA
<213> ORGANISM: Strepto-coccus pneumoniae

<400> SEQUENCE: 15

```
acgttggggg cggttggaat gctgagacct atgcagcggt tgaactgatt gaaagccatt      60
caaccaaaga agagttcatg acggactacc gcctttatat cgaactctta cgcaatctag     120
cagatgaagc aggtttgccg aaaacgcttg atacagggag tttagctgga attaaaacgc     180
acgagtattg cacgaataac caaccaaaca accactcaga ccacgttgac ccttatccat     240
atcttgctaa atgggcatt agccgtgagc agtttaagca tgatattgag aacggcttga     300
```

<210> SEQ ID NO 16
<211> LENGTH: 300
<212> TYPE: DNA
<213> ORGANISM: Strepto-coccus pyogenes

<400> SEQUENCE: 16

```
tcagtgtcaa agaaaaagag ttattgacta aagagcaatt tgataagcta ttgcaggctc      60
ccaatacaac aaccttagct cgactgttgc accagtcagt ctatcaccta actgttgacg     120
atctcaacga tttggatcgg ctagaatcta tcttaatggc tgagctaacc aagacctatc     180
gctgggcttt tgcagaaacc cctcaacctg acatagtaca attatttacc ttgcgttaca     240
cctatcataa tgtcaaagtg ttgttaaaag ctaaagctag tcaagcagat ctgagtcact     300
```

<210> SEQ ID NO 17
<211> LENGTH: 235
<212> TYPE: DNA
<213> ORGANISM: Tropheryma whipplei

<400> SEQUENCE: 17

```
agagagatgg ggtgcaggac agggtttgtt ttgtactgct tgtaacagga tctattagga      60
gagatacatt tgtgttagtt gttacacata cttcttgtgt atttgtatta cttactcttg     120
tgtatttggt aytagatgaa acagatgtag atgaaacaga tgataggagg datagrgcag     180
gaggtgtctg tctggcaaag gctgtttcat attgtaggga tgataggagg agaag         235
```

<210> SEQ ID NO 18
<211> LENGTH: 300
<212> TYPE: DNA
<213> ORGANISM: Acineto-bacter calco-aceticus-baumanii

<400> SEQUENCE: 18

```
gggtcacaag ttcaagtctt gtcagaccca ccatgacttt gactggttga agttatagat      60
aaaagataca tgattgatga tgtaagctgg ggacttagct tagttggtag agcgcctgct     120
ttgcacgcag gaggtcagga gttcgactct cctagtctcc accagaactt aagataagtt     180
cggattacag aaattagtaa ataaagatta agatcttggt ttattaactt ctgtgatttc     240
attatcacgg taattagtgt gatctgacga agacacatta actcattaac agattggcaa     300
```

<210> SEQ ID NO 19
<211> LENGTH: 270
<212> TYPE: DNA
<213> ORGANISM: Acineto bacter lwoffii

<400> SEQUENCE: 19

| | | |
|---|---|---|
| gcctgacagc atgtagccta cccgtttcat ctctcccatc tcaaagcatt tcgactcaag | 60 |
| cgattgccag cttatttgat caggcgcaaa gctctggtgt tttagtgatt cagcgtgatc | 120 |
| aacaagtaca ggtctatggc aatgatttaa atcgtgcaaa taccgaatat gttcccgcct | 180 |
| ctacttttaa aatgctcaat gctctgattg gcctgcaaca tggcaaagcc acaaccaatg | 240 |
| aaattttaa atgggatggc aagaaacgca | 270 |

<210> SEQ ID NO 20
<211> LENGTH: 290
<212> TYPE: DNA
<213> ORGANISM: Entero-bacter aerogenes

<400> SEQUENCE: 20

| | | |
|---|---|---|
| gctggcggta accggtgaaa ccgaaagcac cggtaccatg gtgcgtttct ggccaagcct | 60 |
| ggaaaccttt accaacgtca ctgaattcga atacgaaatc ctggcgaaac gtctgcgcga | 120 |
| gctgtcgttc ctcaactccg gggtctctat ccgcctgcgc gataagcgcg acggcaaaga | 180 |
| agaccatttc cactacgaag gcggcatcaa ggcgtttgtt gagtatctca acaagaacaa | 240 |
| aacgccgatc cacccgaata tcttctattt ctccaccgaa aaagacggta | 290 |

<210> SEQ ID NO 21
<211> LENGTH: 300
<212> TYPE: DNA
<213> ORGANISM: Escherichia coli

<400> SEQUENCE: 21

| | | |
|---|---|---|
| cgtcatggca tcgccattgc cggaacgcac ggcaaaacga caaccaccgc gatggtttcc | 60 |
| agcatctacg cagaagcggg gctcgaccca accttcgtta acggcgggct ggtaaaagcg | 120 |
| gcggggttc atgcgcgttt ggggcatggt cggtacctga ttgccgaagc agatgagagt | 180 |
| gatgcatcgt tcctgcatct gcaaccgatg gtggcgattg tcaccaatat cgaagccgac | 240 |
| cacatggata cctaccaggg cgactttgag aatttaaaac agacttttat taattttctg | 300 |

<210> SEQ ID NO 22
<211> LENGTH: 300
<212> TYPE: DNA
<213> ORGANISM: Haemo-philus influenzae

<400> SEQUENCE: 22

| | | |
|---|---|---|
| tcagggtggg ctggagcatt cgcattagct ttattgctta ttcctatcgt ggtacgcact | 60 |
| acggacaata tgttattact tgtaccaaat aatttacgtg aagcagcggc agctcttggt | 120 |
| tgctctcaat ggcaagttat tatgatgatt tgttatcgag cagctaaatc agggattta | 180 |
| actggcgtgc tattagcagt tgcccgaatt tcaggagaaa ctgcaccgct attatttacc | 240 |
| gctctgtcta atcaatttct atcttggaat atgaatgaac ctatcgcaaa tttacctgta | 300 |

<210> SEQ ID NO 23
<211> LENGTH: 185
<212> TYPE: DNA
<213> ORGANISM: Klebsiella pneumoniae

<400> SEQUENCE: 23

```
agtttctcgc ccagggcaca aatacgacga tattccggcc ccataatgaa ctcgttatcc     60
agcggatagt cggtatccac gccgtgggta cgtacgcgaa taaccggctc aaaatgctgc    120
agttctttgt tctcgtggag atcgaatttc cactggctgc cgtgctgttc tttctcgttc    180
agctc                                                                185
```

<210> SEQ ID NO 24
<211> LENGTH: 220
<212> TYPE: DNA
<213> ORGANISM: Morganella morgani

<400> SEQUENCE: 24

```
catcctgtac ggagactgaa ttrtcattgt gaatggtcac aaygatgtct ttacagtaac     60
cggcgagggc ttcgtcgata gcgttgtcaa caacctcgaa gaccatgtgg tgtaaaccgg    120
ttccgtcatc ggtatcacca atgtacattc ccgggcgttt acgcaccgcg tccagcccct    180
ttaatacttt gatacttgag gagtcatagg tattcgacat                          220
```

<210> SEQ ID NO 25
<211> LENGTH: 300
<212> TYPE: DNA
<213> ORGANISM: Proteus mirabilis

<400> SEQUENCE: 25

```
tgttaatact attctggctg agaaaccaga actttcacaa caaatcgcag caattggtca     60
tcgtattgtt cacggtggcg agaaatttac taaatctgtc gtcattactg acgaagtcat    120
caaaggtatt gaggcggcta ttccatttgc cccattacat aacccagctc accttattgg    180
tattgaagaa gcgcgtaaag ccttccctca tttaattaat aaaatggtgg cagtatttga    240
cactgcattc caccaaacaa tgccagaaga agcttatctg tatgctctgc catacagctt    300
```

<210> SEQ ID NO 26
<211> LENGTH: 300
<212> TYPE: DNA
<213> ORGANISM: Pseudomonas aeruginosa

<400> SEQUENCE: 26

```
atgaccgagt ccgtcctcga ctatatgagc cgccttggcc gcgatgcccg cgccgcctcg     60
cggttgctcg cgcgcgccgc caccgcgcag aagaaccgcg ccctgctggc cgcggccgat    120
gcgctggacg ccgcccgcgc ggagttgtcc cacgccaacg agcaggacct cgccgccggc    180
cgcgccaatg gcctggagcc ggcgatgctg accgcctgg cgctgacccc ggcgcgcatc    240
gacgacatga tcgagggcct gcgccaggtc gccacgctgc ccgacccgat cggcgagatc    300
```

<210> SEQ ID NO 27
<211> LENGTH: 310
<212> TYPE: DNA
<213> ORGANISM: Serratia marcescens

<400> SEQUENCE: 27

```
cctcaagtat caaggtatta aaagggctgg atgcggtgcg caagcgcccg ggcatgtata     60
tcggcgatac cgatgacggc accggtctgc accacatggt attcgaggtt gtggacaacg    120
ctatcgacga agcgctcgcg ggccactgta gygacattca ggtcaccatc catgcygaca    180
actcggtatc ggtrcaggat gacggccgcg gcattccgac cggcattcac ccggaagaag    240
gggtttcagc cgcagaggtc atcatgaccg tgctgcacgc cggcggtaaa ttcgacgaca    300
```
actcctataa                                                                    310

<210> SEQ ID NO 28
<211> LENGTH: 300
<212> TYPE: DNA
<213> ORGANISM: Borrelia burgdorferi

<400> SEQUENCE: 28
acagacgaaa ttaatagaat tgctgatcaa gctcaatata accaaatgca catgttatca      60
aacaaatctg cttctcaaaa tgtaagaaca gctgaagagc ttggaatgca gcctgcaaaa     120
attaacacac cagcatcact ttcagggtct caagcgtctt ggactttaag agttcatgtt     180
ggagcaaacc aagatgaagc tattgctgta atatttatg cagctaatgt tgcaaatctt     240
ttctctggtg agggagctca aactgctcag gctgcaccgg ttcaagaggg tgttcaacag     300

<210> SEQ ID NO 29
<211> LENGTH: 300
<212> TYPE: DNA
<213> ORGANISM: Treponema pallidum

<400> SEQUENCE: 29
cccagttgcg gttcctcatg aattaaaagg gattgcaaag gagaagtttc acttcgtgga      60
agactcccgc gttacggaga ataccaacgg ccttaagaca atgctcactg aggatagttt     120
ttctgcacgt aaggtaagca gcatggagag cccgcacgac cttgtggtag acacggtggg     180
taccggttac cacagccgtt ttggttcgga cgcagaggct tctgtgatgc tgaaaagggc     240
tgatggctct gagctgtcgc accgtgagtt catcgactat gtgatgaact caacacggt     300

<210> SEQ ID NO 30
<211> LENGTH: 300
<212> TYPE: DNA
<213> ORGANISM: Aspergillus flavus

<400> SEQUENCE: 30
tctgacggca aggatagtta caatggctcc tccgatctcc agctggagcg tatgaacgtc      60
tacttcaacg aggtgcgtac ctcaaaattt cagcatctat gaaaacgctt tgcaactcct     120
gaccgcttct ccaggccagc ggaaacaagt atgtccctcg tgccgtcctc gttgatcttg     180
agcctggtac catggacgcc gtccgtgccg gtcccttcgg tcagctcttc cgtcccgaca     240
acttcgtttt cggccagtcc ggtgctggta caactgggc caagggtcac tacactgagg     300

<210> SEQ ID NO 31
<211> LENGTH: 300
<212> TYPE: DNA
<213> ORGANISM: Aspergillus fumigatus

<400> SEQUENCE: 31
atattgaggg tgtgcgctga cacgagattt gacgtatagg acaaggatgg tgatggttag      60 tgacccttttt tccactcctc gaacttcggc ttccatgcga tcatgttcaa acgccgactc     120
acaatatccg gaaatgaccc ktcagtactg ataatatcta tgtttgacta tcaggccaga     180
tcaccaccaa ggaattgggc actgtaatgc gctctctggg ccagaaccct tccgagtcag     240
agctgcaaga tatgatcaac gaggtggatg ctgacaacaa cggcaccatc gatttccccg     300

<210> SEQ ID NO 32
<211> LENGTH: 275
<212> TYPE: DNA

<213> ORGANISM: Aspergillus niger

<400> SEQUENCE: 32

```
cggtgaatca ggccagatca ccaccaagga gctcggcact gtgatgcgct cccttggcca    60
gaacccctcc gagtctgagc ttcaggacat gatcaacgag gttgacgctg acaacaacgg   120
aacgatcgac ttccccggta tgtgttagat ttacgcctgt aaggcggaaa tgcgggctgg   180
attgtgattg acttttgccg ccagaattcc ttaccatgat ggctcgtaag atgaaggaca   240
ccgactccga ggaggaaatc cgcgaggctt tcaag                              275
```

<210> SEQ ID NO 33
<211> LENGTH: 310
<212> TYPE: DNA
<213> ORGANISM: Candida albicans

<400> SEQUENCE: 33

```
ctctaagtgg gtggtaaatt ccatctaaag ctaaatattg gcgagagacc gatagcgaac    60
aagtacagtg atggaaagat gaaaagaact ttgaaagag agtgaaaaag tacgtgaaat   120
tgttgaaagg gaagggcttg agatcagact tggtattttg catgytgctc tctcgggggc   180
ggccgctgcg gtttaccggg ccagcatcgg tttggagcgg caggataatg gcggaggaat   240
gtggcacggc ttctgctgtg tgttatagcc tctgacgatr ctgccagcct agaccgagga   300
ctgcggtttt                                                          310
```

<210> SEQ ID NO 34
<211> LENGTH: 277
<212> TYPE: DNA
<213> ORGANISM: Candida dubliniensis

<400> SEQUENCE: 34

```
aacttacaac caaatttttt ataaacttgt cacgagatta tttttaatag tcaaaacttt    60
caacaacgga tctcttggtt ctcgcatcga tgaagaacgc agcgaaatgc gatacgtaat   120
atgaattgca gatattcgtg aatcatcgaa tctttgaacg cacattgcgc cctctggtat   180
tccggagggc atgcctgttt gagcgtcgtt tctccctcaa accctagggg tttggtgttg   240
agcaatacga cttgggtttg cttgaaagat gatagtg                            277
```

<210> SEQ ID NO 35
<211> LENGTH: 216
<212> TYPE: DNA
<213> ORGANISM: Candida glabrata

<400> SEQUENCE: 35

```
gtgtcagttc tttgtaaagg gtgctcgaag agtcgagttg tttgggaatg cagctctaag    60
tgggtggtaa attccatcya agctaaata caggcgagag accgatagcg aacaagtaca   120
gtgatggaaa gatgaaaaga actttgaaaa gagagtgaaa aagtacgtga aattgttgaa   180
agggaagggc atttgatcag acatggtgtt ttgcgc                             216
```

<210> SEQ ID NO 36
<211> LENGTH: 198
<212> TYPE: DNA
<213> ORGANISM: Candida tropicalis

<400> SEQUENCE: 36

```
gttataacta aaccaaactt tttatttaca gtcaaacttg atttattatt acaatagtca    60
aaactttcaa caacggatct cttggttctc gcatcgatga agaacgcagc gaaatgcgat   120
```

```
acgtaatatg aattgcagat attcgtgaat catcgaatct ttgaacgcac attgcgccct    180
ttggtattcc aaagggca                                                 198

<210> SEQ ID NO 37
<211> LENGTH: 300
<212> TYPE: DNA
<213> ORGANISM: Candida parapsio-losis (sensu lato)

<400> SEQUENCE: 37
cccagaccta tgtaaagttc cttcgaagag tcgagttgtt tgggaatgca gctytaagtg     60
ggtggtaaat tccatctaaa gctaaatatt ggcgagagac cgatagcgaa caagtmcagt    120
gatggaaaga tgaaaagaac tttgaaaaga gagtgaaaaa gtacgtgaaa ttgttgaaag    180
ggaagggctt gagatcagac ttggtatttt gtatgttact ctytcggggg tggcctctac    240
agtttaccgg ccagcatca gtttgrgcgg taggabaakt gcaaagaaat gtggcactgc     300

<210> SEQ ID NO 38
<211> LENGTH: 275
<212> TYPE: DNA
<213> ORGANISM: Fusarium spp.

<400> SEQUENCE: 38
ccgagttgta atttgtagag gatrcttttg ryrmggtgcc ttccgagtwc cctggaacgg     60
gacgccatag agggtgagag ccccgtctgg ttggayrccr adyctctgta aagytccttc    120
racgagtcga gtagtttggg aatgctgctc taaatgggag gtatatgtct tctaaagcta    180
aatacyggcc agagaccgat agcgcacaag tagagtgatc gaaagatgaa aagmactttg    240
aaaagagrgt taaamagyac gtgaaattgt tgaaa                              275

<210> SEQ ID NO 39
<211> LENGTH: 300
<212> TYPE: DNA
<213> ORGANISM: Fusarium solani

<400> SEQUENCE: 39
gccgttgttg tcggcgtcga cctcgttgat catgtcctga agctcagact cggaggggtt     60
ctggccgagg gagcgcatga cggtgcccag ctccttggtg gtgatctggc ctagagcgaa    120
acgtttagtt taccgtctcg aaacgattcg catcgactga agagcagtgt gcgcatagag    180
gttcgatgca tcatgtaatt cggaaaagga atcgggctga ggccgacgag gggctttgcg    240
agcaggaggg agaatcactc accatcgcca tccttgtcct atgcaagagg ttagcgacag    300

<210> SEQ ID NO 40
<211> LENGTH: 300
<212> TYPE: DNA
<213> ORGANISM: Cytomegalo-virus

<400> SEQUENCE: 40
tctcagacac tggctcagac ttgacagaca cagtgtcctc ccgctcctcc tgagcaccct     60
cctcctgttc ctcatcactc tgttcacttt cttcctgatc actgttctca gccacaatta    120
ctgaggacag agggatagtc gcgggtacag gggactctgg aggtgacacc agagaatcag    180
aggagctggc accagcggtg gccaaagtgt aggctacaat agcctcttcc tcatctgact    240
cctcggcgat ggcccgtagg tcatccacac taggagagca gactctcaaa ggatcggccc    300

<210> SEQ ID NO 41
```

```
<211> LENGTH: 300
<212> TYPE: DNA
<213> ORGANISM: Epstein-barr virus

<400> SEQUENCE: 41
gacatagagg gggttgaggt ctacgagttc ccatcggagc tggacatgct ctacgccttc      60
ttccagctca tcagagacct cagcgtggag attgtgaccg ctacaacgt ggccaacttt     120 gactggccct acattctgga cagagccagg cacatctaca gcatcaaccc agcctctctg    180
ggcaaaatta gggctggggg cgtctgcgag gtcaggcgac ccatgatgc gggcaagggc     240 ttcttgcggg ccaacaccaa ggtccgcatc accggcctca tccccatcga catgtacgcc    300

<210> SEQ ID NO 42
<211> LENGTH: 300
<212> TYPE: DNA
<213> ORGANISM: Herpes simplex

<400> SEQUENCE: 42
agctctcgag ctacaagctc aacgccgtgg ccgaagccgt cctgaaggac aagaagaagg     60
acctgagcta tcgcgacatc cccgcctact acgccaccgg gcccgcgcaa cgcggggtga    120
tcggcgagta ctgcatacag gattccctgc tggtgggcca gctgttttt aagttttgc      180 cccatctgga gctctcggcc gtcgcgcgct tggcgggtat taacatcacc cgcaccatct    240
acgacggcca gcagatccgc gtctttacgt gcctgctgcg cctggccgac agaagggct    300

<210> SEQ ID NO 43
<211> LENGTH: 300
<212> TYPE: DNA
<213> ORGANISM: Herpes simplex

<400> SEQUENCE: 43
ggcggcgtct gggttttttg ccccccacaa ccccgggga ccacccaga cggcaccgcc       60 gccttgccgc cggcagaact tctacaaccc ccacctcgct cagaccggaa cgcagccaaa    120
ggccctcggg ccggctcagc gccatacgta ctacagcgag tgcgacgaat ttcgatttat    180
cgccccgcgt tcgctggacg aggacgcccc cgcggagcag cgcaccgggg tccacgacgg    240
ccgcctccgg cgcgccccta aggtgtactg cgggggggac gagcgcgacg tcctccgcgt    300

<210> SEQ ID NO 44
<211> LENGTH: 300
<212> TYPE: DNA
<213> ORGANISM: Herpes simplex

<400> SEQUENCE: 44
aagtggaact gcttggtggc ggatggctag tgtgcctatt aatgcttatt tcgaaagaga    60
tatagccttt ttatttaacc ctcgatgcgt tatcgagact gccctgggt ctaagatatt     120 atgtcgatac aataaaaata ttggtgttgt gtttgtggac aatgatacta cgtgtaatgt    180
ttcctttccg agcggtgtgc agttacaatt actaaatcaa tcggtgatgg agtcaattag    240
aactaaaacg tatgtagtgg attacgctag gaaaactaca gagagaggtg attgcttcat    300

<210> SEQ ID NO 45
<211> LENGTH: 300
<212> TYPE: DNA
<213> ORGANISM: Varicella zoster

<400> SEQUENCE: 45
ggatacgtcg cggggcccccg gcgcgttttg tactccgggt tgggagatcc acccggccag    60
```

```
gctcgttgag gacatcaacc gtgttttttt atgtattgca cagtcgtcgg gacgcgtcac    120
gcgagattca cgaagattgc ggcgcatatg cctcgacttt tatctaatgg gtcgcaccag    180
acagcgtccc acgttagcgt gctgggagga attgttacag cttcaaccca cccagacgca    240
gtgcttacgc gctactttaa tggaagtgtc ccatcgaccc cctcgggggg aagacgggtt    300

<210> SEQ ID NO 46
<211> LENGTH: 774
<212> TYPE: DNA
<213> ORGANISM: Toxoplasma gondii

<400> SEQUENCE: 46
tttgcatagg ttgcagtcac tgacgagctc ccctctgctg gcgaaaagtg aaattcatga     60
gtatctgtgc aactttggtg tattcgcaga ttggtcgcct gcaatcgata gttgaccacg    120
aacgctttaa agaacaggag aagaagatcg tgaaagaata cgagaagagg tacacagaga    180
tagaagtcgc tgcggagaca gcgaagactg cggatgactt cactcccgtc gcaccagcag    240
cagaggagtg ccgggcaaga aaatgagatg cctagaggag acacagcgtg ttatgaacaa    300
atctattgag gtttcgcgaa gaggagggaa catattatat acagaagaag aacaagagac    360
gtgccgcatg tcgctaagcc atcggaaggg atgctcagaa aatggcacag tatcacatta    420
cagttccgtt gattcgtctg atggtgacga aaggggaaga atagttgtcg caccaaaact    480
sgctagttgt tayttttgaag aagacgagag atggagtgaa ccaccaaaaa tcggagaaaa    540
tcgatggtgt cacgttttttt gtcagacttc actttgtgca gaagcattgc ccgtccaaac    600
tgcaacaact gctctagcgt gttcgtctcc attccgtaca gtcttcaaaa atacaaaaga    660
gaacattcca gcaacttctr cctttgttct tttagcctca atagcaggat gacgcctccc    720
tcctatcttt cagccaaccc agcaaacacc gacgaactct ctgtagagta acaa          774

<210> SEQ ID NO 47
<211> LENGTH: 299
<212> TYPE: DNA
<213> ORGANISM: Staphylo-coccus epidermidis ica

<400> SEQUENCE: 47
tacagttgcc ttatttattg acagtcgcta cgaaaagaaa aatatagttg gcctgatatt     60
tttaagttgg tatccaacgt tatactgggt tatcaatgcc gcagttgtca ttatggcatt    120
tcctaaagca ttaaaaagaa agaaaggtgg ctatgctaca tggtcaagcc cagacagagg    180
caatatccaa cggtaacctc ttatttaaat atagttaggg agagcttatt tattactata    240
tccggagtat tttggatgta ttgtatcgtt gtgatgattg tttatatagg aactcttat     299

<210> SEQ ID NO 48
<211> LENGTH: 300
<212> TYPE: DNA
<213> ORGANISM: Staphylo-coccus aureus

<400> SEQUENCE: 48
tgaaaaatga ttatggctca ggtactgcta tccaccctca aacaggtgaa ttattagcac     60
ttgtaagcac accttcatat gacgtctatc catttatgta tggcatgagt aacgaagaat    120
ataataaatt aaccgaagat aaaaaagaac ctctgctcaa caagttccag attacaactt    180
caccaggttc aactcaaaaa atattaacag caatgattgg gttaaataac aaaacattag    240
acgataaaac aagttataaa atcgatggta aaggttggca aaaagataaa tcttggggtg    300
```